United States Patent
Wan et al.

(10) Patent No.: US 12,403,106 B2
(45) Date of Patent: Sep. 2, 2025

(54) PROPHYLACTIC SKIN TREATMENT FOR RADIATION THERAPY

(71) Applicant: THE BOARD OF TRUSTEES OF THE LELAND STANFORD JUNIOR UNIVERSITY, Stanford, CA (US)

(72) Inventors: Derrick C. Wan, Stanford, CA (US); Michael T. Longaker, Stanford, CA (US); Geoffrey C. Gurtner, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 678 days.

(21) Appl. No.: 17/778,802

(22) PCT Filed: Oct. 20, 2020

(86) PCT No.: PCT/US2020/056421
§ 371 (c)(1),
(2) Date: May 20, 2022

(87) PCT Pub. No.: WO2021/101646
PCT Pub. Date: May 27, 2021

(65) Prior Publication Data
US 2022/0409559 A1    Dec. 29, 2022

Related U.S. Application Data

(60) Provisional application No. 62/938,209, filed on Nov. 20, 2019.

(51) Int. Cl.
| | |
|---|---|
| *A61K 31/16* | (2006.01) |
| *A61K 9/00* | (2006.01) |
| *A61P 17/02* | (2006.01) |

(52) U.S. Cl.
CPC .............. *A61K 31/16* (2013.01); *A61P 17/02* (2018.01); *A61K 9/0014* (2013.01)

(58) Field of Classification Search
CPC ........... A61K 31/16; A61P 17/02; A61P 17/16
See application file for complete search history.

(56) References Cited

U.S. PATENT DOCUMENTS

| | | |
|---|---|---|
| 9,737,395 B2 | 8/2017 | Nguyen et al. |
| 2009/0069623 A1 | 3/2009 | Oh |
| 2009/0198332 A1 | 8/2009 | Becker |
| 2009/0305963 A1 | 12/2009 | Sukhatme et al. |
| 2010/0068279 A1 | 3/2010 | Hartwell |
| 2011/0150962 A1 | 6/2011 | Lutz et al. |
| 2012/0220651 A1 | 8/2012 | Chevion et al. |
| 2013/0289235 A1 | 10/2013 | Daniloff et al. |
| 2014/0039069 A1 | 2/2014 | Desai et al. |
| 2017/0281570 A1 | 10/2017 | Gurtner et al. |
| 2017/0305967 A1 | 10/2017 | Szeto et al. |
| 2017/0319756 A1 | 11/2017 | Pulapura et al. |

FOREIGN PATENT DOCUMENTS

| | | |
|---|---|---|
| WO | 2006020727 | 2/2006 |
| WO | 2013093868 | 6/2013 |

OTHER PUBLICATIONS

Li, et al. "Research progress on radiation-induced skin damage" Chinese J. of Clinical Physicians (2013), vol. 7:6, pp. 2650-2652.
PCT/US20/56421 Written Opinion of the International Searching Authority, Feb. 23, 2021.
Flacco et al., "Deferoxamine Preconditioning of Irradiated Tissue Improves Perfusion and Fat Graft Retention", Plast Reconstr Surg. 2018, vol. 141, No. 3, Mar. 2018 (Mar. 1, 2018), pp. 655-665*.
Shen et al., "Prophylactic treatment with transdermal deferoxamine mitigates radiation-induced skin fibrosis", Sci Rep, vol. 10, No. 12346, Jul. 23, 2020 (Jul. 23, 2020), pp. 1-11.
Alexis Donneys, et al. "Targeting angiogenesis as a therapeutic means to reinforce osteocyte survival and prevent nonunions in the aftermath of radiotherapy" Head and Neck (2014) vol. 37, No. 9:1261-1267.
Alicia Snider, et al. "Topical Deferoxamine Alleviates Skin Injury and Normalizes Atomic Force Microscopy Patterns Following Radiation in a Murine Breast Reconstruction Model" Annals of Plastic Surgery (2018) vol. 81, No. 5: 604-608.
Mimi Borelli, et al. "Outcomes of Fat Grafting in Irradiated Tissue are Improved by Pre-Treatment with Transdermal Deferoxamine" J. Amer. Coll. of Surgeons (2019) vol. 229, No. 4.

*Primary Examiner* — Sahar Javanmard
(74) *Attorney, Agent, or Firm* — Rimon PC

(57) ABSTRACT

Methods of reducing skin fibrosis by prophylactically treating skin prior to radiation therapy are described herein. The methods include applying an effective amount of DFO to skin that may be subjected to radiation, e.g., during treatment for cancer at a treatment site. The DFO may be administered transdermally.

9 Claims, 14 Drawing Sheets

DFO Treated　　　　　　　　Saline Treated
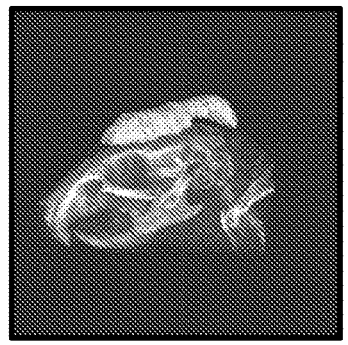 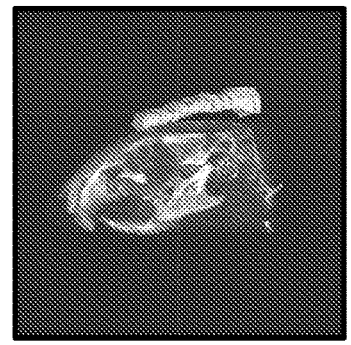
FIGURE 3A　　　　　　　　FIGURE 3B
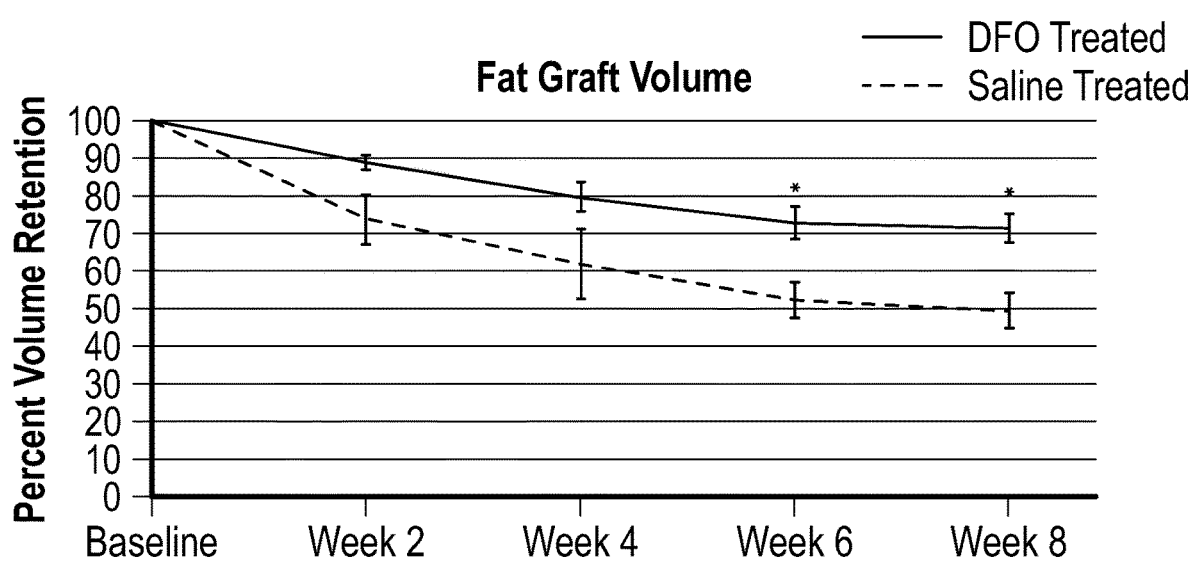
FIGURE 3C

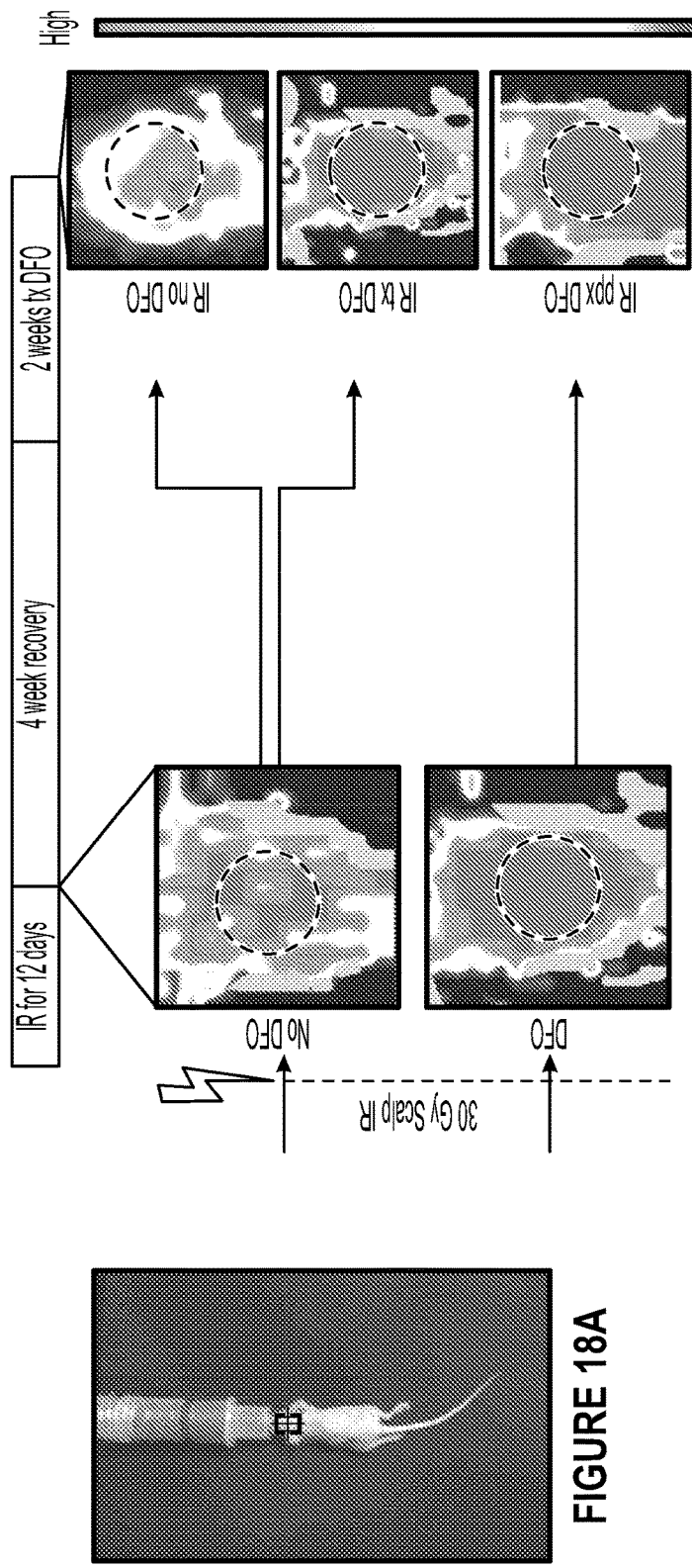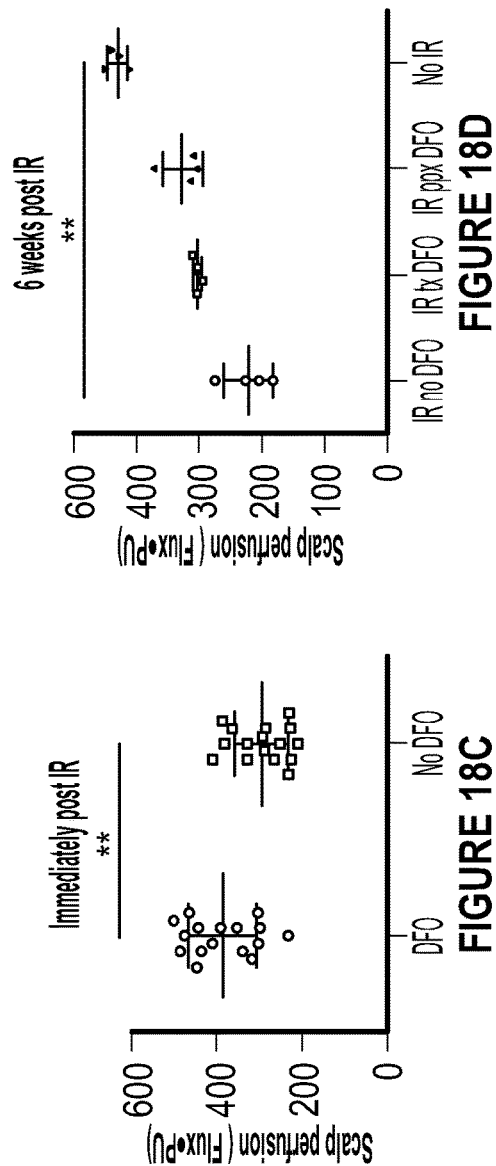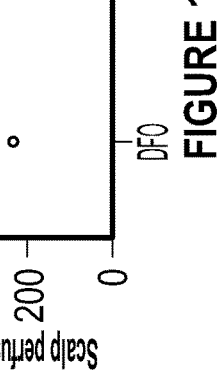
FIGURE 18A
FIGURE 18B
FIGURE 18C
FIGURE 18D

PROPHYLACTIC SKIN TREATMENT FOR RADIATION THERAPY

CROSS REFERENCE TO RELATED APPLICATIONS

This application claims the benefit of U.S. Application No. 62/938,209, filed Nov. 20, 2019, which is herein incorporated by reference in its entirety.

STATEMENT AS TO FEDERALLY SPONSORED RESEARCH

This invention was made with Government support under contract DE026914 awarded by the National Institutes of Health. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

After heart disease, cancer remains the leading cause of death in the United States, with an estimated 1.6 million new cancer cases diagnosed and 600,000 cancer-related deaths projected for 2017. However, in recent years, substantial progress in medical care has been made, with surgery, chemotherapy, and radiation therapy increasing both the number of cancer survivors and the length of their survival. With this improvement, long-term issues related to treatment of cancer, such as with radiation therapy, have become increasingly apparent, and have been shown to profoundly impact quality of life. Radiation-induced soft tissue injury is one of the most common side effects of radiotherapy, affecting over 90% of patients, and the resulting soft tissue atrophy and fibrosis can lead to both severe cosmetic and long-term functional impairment.

Radiation therapy is a mainstay in the treatment of many malignancies. Radiation therapy can cause collateral damage to surrounding tissue, however, with resultant hypovascularity, fibrosis, and atrophy, and the damaged tissue can be difficult to reconstruct. Radiation therapy (RT) is inevitably associated with a pathological level of progressive skin fibrosis.

Over 5.6 million soft tissue reconstructive procedures are performed annually in the United States, with the majority related to tumor extirpation and sequelae of adjuvant radiation therapy. Even with intact overlying epithelium, insufficient underlying soft tissue results in visible asymmetry and contour abnormalities, and may also contribute to unstable wounds and inadequate protection of critical organs and structures including bone, implanted hardware, and large vessels. While radiation therapy has been shown to be incredibly effective at reducing local recurrence risk for various tumors, collateral damage to adjacent soft tissue resulting in obliteration of microvasculature and fibrosis may significantly complicate reconstructive strategies.

Chronic radiation injury is characterized by epidermal thinning, eosinophilic homogenized sclerosis of dermal collagen, scattered large and atypical fibroblasts, and fibrous thickening with luminal obliteration of deep vessels. Vascular damage and development of fibrosis is thought to result from radiation-induced cytokine expression, generation of reactive oxygen species, and cellular apoptosis, and soft tissue reconstruction of such hostile sites remains extremely challenging. While autologous fat grafting has become increasingly popular to address post-radiation soft tissue deficits, fibroinflammatory changes and hypovascularity have been associated with poorer fat graft outcomes. Improved retention has been noted with cell assisted lipotransfer, but the functional heterogeneity among stromal cells used to enrich lipoaspirate, in concert with concerns regarding post-oncologic locoregional recurrence, has limited the wide-spread adoption of this strategy. Deferoxamine (DFO) is an FDA-approved iron chelating medication for acute iron intoxication and chronic iron overload that has also been shown to increase angiogenesis. DFO has been demonstrated to increase hypoxia-inducible factor-1 alpha (HIF-1a) activity and enhance expression of angiogenic growth factors. Studies have also shown local injection of DFO to improve ischemic flap survival in both mouse and pig models, with increased skin flap blood perfusion and capillary density noted in DFO-treated animals. Furthermore, in the setting of irradiated bone, multiple reports have found DFO to promote bone regeneration following distraction osteogenesis through enhanced vascularity.

The potential of DFO as an angiogenic and antioxidant agent with the potential to improve fat graft survival in healthy subjects has also been studied, and its use to increase the viability of fat grafts for plastic surgery has been proposed. Importantly, DFO was recently suggested to promote fat graft viability in a rat model. However, more inflammation and fibrosis was noted in DFO injected fat grafts, though no change in cellular apoptosis was appreciated. Repeated manipulation of fat grafts with each injection may have contributed to this observation. In addition, adipogenic differentiation of resident stromal cells has been purported to contribute to long-term fat graft retention, and direct exposure of DFO to fat grafts may be detrimental to this process. Studies have shown intracellular iron deficiency through DFO administration to severely blunt adipocyte differentiation. These findings thus temper enthusiasm for direct injection of DFO into fat grafts.

Current treatment options for radiation-induced fibrosis (RIF) are limited. The iron chelator deferoxamine (DFO) has previously been shown to improve skin vascularization when injected into radiated tissue prior to fat grafting. Applicant describes methods of topical delivery of DFO prior to and immediately following irradiation which can mitigate the chronic effects of radiation damage to the skin.

SUMMARY OF THE DISCLOSURE

A method of decreasing radiation induced fibrosis is provided, the method including: administering an effective amount of DFO to a region of skin of a subject at a treatment site for a first period of time prior to a radiation treatment; administering an effective amount of DFO to the region of skin during a second period of time; administering radiation to the region of skin during the second period of time; and administering an effective amount of DFO to the region of skin for a third period of time subsequent to the radiation treatment.

In some variations, administering the effective amount of DFO to the region of skin may include delivering DFO transdermally. Administering the effective amount of DFO to the region of skin may include applying a transdermal delivery device to a surface of the region of skin at the treatment site. In some variations, the transdermal delivery system may include DFO encapsulated in reverse micelles.

In some variations, applying the transdermal delivery device to the surface of the region of skin at the treatment site may further include applying a new transdermal delivery device at a selected interval of time during each of the first, second and third periods of time. The selected interval of time may be about 12 hours to about 36 hours. In some variations, the selected interval of time is daily.

In some variations, the first period of time may be about 3 days to about 21 days. In some variations, the second period of time may be about 5 days to about 10 weeks. In some variations, the third period of time may be about 2 weeks to about 8 weeks, or more.

In some variations, administering the radiation during the second period of time further comprises administering the radiation in a pattern of administering radiation for a first portion of the second period of time and subsequently not administering radiation for a second portion of the second period of time. In some variations, the pattern of administering radiation and subsequently not administering radiation may be repeated about 3 to 10 times during the second period of time. In some variations, the first portion of time during the second period of time is about 3 days to about 7 days, and the second portion of time is about 4 days to about 10 days.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A-B are representative three-dimensional reconstructions of fat grafts after eight weeks in either DFO (FIG. 3A) or saline (FIG. 3B) preconditioned irradiated scalp.

FIG. 3C shows that quantification of fat graft volumes revealed significantly increased retention in fat grafts placed into DFO treated scalp (upper line) when compared to saline treated scalp (lower line) after six and eight weeks (*p<0.05).

FIG. 6 shows a Laser Doppler Analysis following fat grafting.

FIG. 7-10 show an evaluation of irradiated scalp histology following fat grafting.

FIG. 8 shows that a quantification of dermal thickness demonstrated significant increase following radiation, with no difference between saline or DFO treated skin. Both treatment groups demonstrated significant reduction following fat grafting (*p<0.05).

FIGS. 9A-E show representative picrosirius red stained sections at 20× magnification demonstrating density of positive-stained collagen after irradiation and saline or DFO preconditioning, followed by fat grafting. Scale bar represents 100 µm. FIG. 10 shows that a quantification of collagen content revealed significant increase in collagen following radiation, irrespective of saline or DFO treatment. Both groups demonstrated significant reduction following fat grafting (*p<0.05).

Group 4 mice (row 4 of FIG. 4) no irradiation and no DFO (No IR). (n=4/group).

FIG. 18A is a photographic representation of a CD1 Nude mouse prepared for Laser Doppler Analysis (LDA) with the region of interest (ROI) represented by the overlying white box. Laser Doppler Analysis (LDA) of irradiated mouse scalps. FIG. 18B is a graphical presentations of representative heat maps of mouse scalps showing perfusion immediately following irradiation (left; without [top] and with DFO [bottom] prophylactic DFO TDDS treatment) and 6 weeks after irradiation (right). Black/dark blue colors represent lower perfusion and yellow/red colors represent higher perfusion. FIGS. 18C and 18D show Quantification of the laser Doppler perfusion index immediately following irradiation (18C) and 6 weeks after irradiation (18D). The abbreviations in FIGS. 18A-18C are as follows: DFO—deferoxamine, Gy—gray, IR—irradiation, ppx—prophylactic, tx—therapeutic.

DETAILED DESCRIPTION

Figure 1:
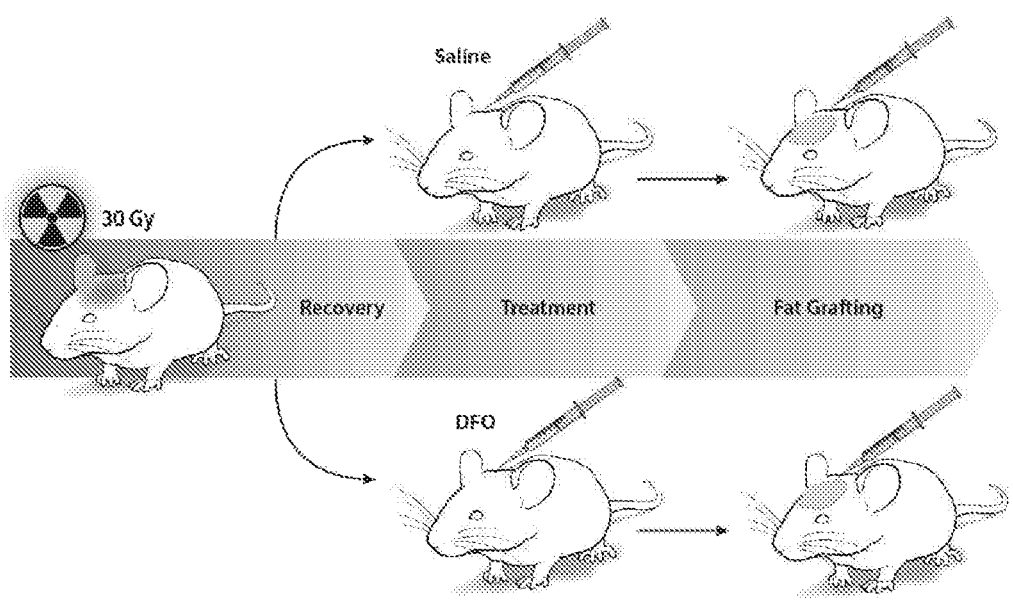
FIG. 1 shows a schematic of an irradiated tissue treatment according to this invention.

It is estimated that by 2019 two million new patients in the United States will be diagnosed with cancer, and more than half of these patients will eventually receive radiation therapy (RT). With increasing survival rates, the late effects of cancer treatments are becoming even more apparent. Fibrotic skin damage is the most important dose-limiting factor in RT administration. The skin is extremely sensitive to RT, and more than 95% of patients experience acute skin reactions. Acute skin damage inevitably progresses, over weeks to years, to radiation-induced skin fibrosis (RIF), characterized by dermal induration and microvascular thickening, leading to hypoperfusion and hypoxia. When RIF is severe, significant cosmetic and functional consequences may result which can substantially impact quality of life, including loss of range of motion and muscle strength. The pathogenesis of RIF is multifactorial and remains incompletely understood. Key factors contributing to excessive soft tissue fibrosis include the generation of free radicals, activation of fibroblasts, and damage to microvascular endothelial cells.

Current treatments for RIF are limited, with few having shown significant benefit in well-designed clinical trials, and no effective prophylactic regimen exists to mitigate this complication. Pentoxifylline, a methylxanthine derivative originally developed to improve blood flow in cardiovascular patients, 11 also decreases RIF and improves tissue function, especially when used in combination with vitamin E. The beneficial actions of pentoxifylline are thought to be driven largely by its ability to enhance locoregional blood flow, decrease blood viscosity and systemic vascular resistance, and thus reduce tissue hypoxia. Despite this reported benefit, a significant number of patients experience severe side effects, and poor tolerance and compliance significantly limit the use of pentoxifylline clinically.

The present invention provides a method to prophylactically minimize long term development of skin fibrosis, leading to scarring and limitation of physical function, in partients undergoing radiotherapy (RT) for cancer, by administration of deferoxamine. In some variations, this method may be performed in combination with autologous fat grafting.

It has been demonstrated that subcutaneous injections of deferoxamine (DFO) prior to fat grafting enhances soft tissue vascularity and subsequent graft retention in previously irradiated sites. DFO is a United States Food and Drug Administration (FDA)-approved agent commonly used to treat conditions associated with iron overload. Through its iron-chelating mechanisms, DFO stabilizes hypoxia-inducible factor-1 alpha (HIF1a), which translocates to the nucleus and acts as a transcription factor for a number of potent pro-angiogenic genes, including vascular endothelial grmvth factor (VEGF) and endothelial nitric oxide synthase. The downstream result is improved tissue vascularization. Numerous studies have found that DFO treatment improves vascularization in states of tissue hypoxia, including those associated with skin flaps, irradiated bones, and diabetic foot ulcers. Radiation damage in the skin is a slow progressive process that is particularly difficult to reverse when complete. As such, ideal treatment regimens would either be prophylactic in nature or target the earliest stages of this pathologic process. Topical DFO treatment using a novel transdermal drug delivery system (TDDS) prior to and immediately following irradiation may improve tissue vascularity and mitigate the downstream severity of late, chronic RIF within the skin.

Skin fibrosis and its long-term sequelae are frequent and often unavoidable side effects for most patients treated with RT. In addition to aesthetic concerns, this may significantly alter tissue form and function, with a profound impact on patient quality of life. RIF is a progressive disease that worsens over months and years following radiation treatment. As such, preventing RIF prior to RT, or treatments targeting the earliest stages of its development, may prevent later downstream amplification and thus provide the most therapeutic benefit. Applicant has discovered that topical administration of DFO can increase skin vascularization and perfusion, thereby mitigating one key aspect of RIF. The most beneficial effects may be obtained in the methods described herein for prophylactic DFO treatment, administered before, during, and after irradiation.

A major mechanism by which RIF manifests in the skin is through damage to the irradiated microvasculature. In the first 24 hours following RT, leukocytes infiltrate blood vessels and fibrin plugs form. The endothelial cells which line blood vessels subsequently swell and undergo hyperplasia, leading to perivascular fibrosis, small vessel obliteration, hypoperfusion, and ultimately tissue hypoxia, Conditions of low oxygen tension stimulate increased expression of collagen type 1 alpha 1 (COL1A1) and promote the development of tissue fibrosis. Laser Doppler imaging may be used as a surrogate measure of vessel density, in addition to CD31 staining to show that radiation significantly reduces skin blood flow. It has been previously shown that subcutaneous injections of DFO into irradiated tissue prior to fat grafting can increase perfusion in the overlying skin and thereby mitigate the fibrosing effects of RT. Applicants show here, for the first time, that topical DFO administration via a novel TDDS can confer significant benefit when the skin is conditioned prior to RT.

It is likely that the protective role of DFO may relate to its downstream pro-angiogenic effects. DFO is an FDA-approved iron chelator which has shown recent benefit in the setting of ischemic and irradiated tissue. DFO chelates iron which leads to elevated HIFI (I and thus increased expression of a number of potent pro-angiogenic genes like VEGF. Prophylactically treating patients with DFO can result in significant benefits to scalp perfusion in the immediate post-RT period. Furthermore, prophylactic treatment may be significantly more effective than post-radiation treatment alone. Since RT is an elective treatment, often planned weeks or months in advance, targeting the skin during this early time window is clinically feasible, and even moderate mitigation of skin fibrosis may have profound translational benefit for cancer patients.

Accordingly a method of decreasing radiation induced fibrosis is provided herein, the method including: administering an effective amount of DFO to a region of skin of a subject at a treatment site for a first period of time prior to a radiation treatment; administering an effective amount of DFO to the region of skin during a second period of time; administering radiation to the region of skin during the second period of time; and administering an effective amount of DFO to the region of skin for a third period of time subsequent to the radiation treatment.

Administering the effective amount of DFO to the region of skin may include delivering DFO transdermally. Administering the effective amount of DFO to the region of skin may include applying a transdermal delivery device to a surface of the region of skin at the treatment site. In some variations, the administering the effective amount if DFO may include a region of skin surrounding the region of skin at the treatment site. An area of the surrounding region of skin may be about 5%, 10%, 25%, 50%, or more than an area of the region of skin at the treatment site. In some variations, the transdermal delivery system may include DFO encapsulated in reverse micelles.

Applying the transdermal delivery device to the surface of the region of skin at the treatment site may further include applying a new transdermal delivery device at a selected interval of time during each of the first, second and third periods of time. The selected interval of time may be about 12 hours, about 14 hours, about 16 hours, about 18 hours, about 20 hours, about 24 hours, about 28 hours, about 32 about, about 36 hours, about 48 hours, or any number of hours therebetween. In some variations, the selected interval of time is daily.

In some variations, the first period of time may be about 3 days, about 5 days, about 7 days, about 10 days, about 14 days, about 18 days, about 21 days, or any number of days therebetween. In some variations, the second period of time may be about 5 days to about 10 weeks. In some variations, the third period of time may be about 2 weeks, about 3 weeks, about 4 weeks, about 6 weeks, about 8 weeks, or more.

In some variations, administering the radiation during the second period of time further comprises administering the radiation in a pattern of administering radiation for a first portion of the second period of time and subsequently not administering radiation for a second portion of the second period of time. In some variations, the pattern of administering radiation and subsequently not administering radiation may be repeated about 3, about 4, about 5, about 6, about 7 about 8, about 9, about 10 times, or more during the second period of time. In some variations, the first portion of time during the second period of time is about 3 days, about 4 days, about 5 days, about 6 days, or about 7 days, and the second portion of time is about 4 days, about 5 days, about 6 days, about 7 days, about 8 days, about 9 days, about 10 days or more.

Another aspect of the invention provides a method of preconditioning irradiated soft tissue site with DFO to enhance vascularity prior to implantation of a fat graft. HIF-1a is typically degraded by prolyl hydroxylase domain-containing protein 2 (PHD2). DFO, through chelation of the iron co-factor for PHD2 activity, has been shown to stabilize HIF-1a, leading to an increase in downstream angiogenic factors and recruitment of endothelial progenitor cells.

This is the mechanism by which DFO has been thought to promote revascularization of ischemic skin flaps, enhance wound healing in diabetic mice, and augment callus size, mineralization, and mechanical strength at irradiated bone injury sites. Furthermore, reversal of radiation induced hypovascularity has also been appreciated with DFO treatment during mandibular distraction osteogenesis. All of these findings support the potential for DFO, through stabilization of HIF-1a and increased angiogenic gene expression, to precondition the irradiated recipient site for subsequent fat grafting.

Preconditioning the irradiated tissue at the fat graft site with DFO before implantation of the fat graft facilitates earlier revascularization of the fat graft. Histologic analysis of treated skin according to this method has revealed increased vascularity, which translates to enhanced volume retention, when fat grafts were placed into DFO preconditioned recipient sites. Interestingly, the addition of fat grafts to DFO treated irradiated tissue leads to further improvement in vascularity, even though DFO-related effects might plateau after four treatments. This suggests that alternative mechanisms may also be employed by transferred adipocytes and associated stromal cells to improve vascularity following fat grafting. Finally, the effects of DFO treatment on skin vascularity are not associated with significant changes to dermal thickness and collagen content, compared to decreased dermal thickness and collagen content following fat grafting. The architectural changes observed in the dermis with decreased collagen secondary to fat transfer may not necessarily be a result of improved vascularity alone. In patients with radiation fibrosis and soft tissue atrophy, preconditioning tissue with serial DFO injections prior to fat grafting may be difficult logistically and not well tolerated by patients. Transdermal delivery of DFO to irradiated tissue prior to and/or after fat graft implantation may be used as an alternative to delivery of DFO via direct injection. Such an approach may also be potentially effective at preconditioning irradiated tissue for fat grafting and would likely be better tolerated by patients. Alternatively, nanoparticle formulations of DFO have also been developed, and their controlled release of DFO may similarly be employed to improve vascularity of irradiated skin. These nanoparticles may also be directly injected with fat grafts to promote earlier revascularization.

As DFO promotes expression of multiple angiogenic factors through stabilization of HIF-1a, concern may also be raised regarding its use in irradiated post-oncologic resection sites. Though no studies, to our knowledge, have demonstrated an increased risk for cancer recurrence following local administration of DFO, several reports have suggested an anti-tumor effect. Iron is necessary for oxygen transport, cell metabolism, and growth, and it is especially important in cells with active growth. Not surprisingly, iron chelators such as DFO have been found to reduce liver fibrosis, and its effect on iron metabolism has been shown to clinically reduce progression of hepatocellular carcinoma. Iron dependency has also been reported in human epidermal growth factor receptor 2 positive breast cancer cells, and multiple breast cancer cell lines have been shown to be vulnerable to iron chelation. These reports thus suggest local DFO application may not be associated with increased risk for cancer recurrence.

DFO treatment can improve radiation-induced hypovascularity, and this enhanced perfusion may improve the quality of the recipient site for fat grafting. Following DFO treatment, long-term retention of fat grafts injected into irradiated sites was significantly improved.

Reconstruction of irradiated tissue remains challenging owing to radiation induced alterations to the recipient bed. Fibroinflammatory changes and hypovascularity have been shown to impact fat graft retention, and while cell-based strategies have been shown to improve outcomes, regulatory and safety concerns have, to date, limited their translational potential. As an alternative approach, preconditioning irradiated tissue with deferoxamine improves local perfusion, which is associated with improved radiographic and histologic fat graft outcomes. Preconditioning with deferoxamine prior to fat grafting therefore holds promise for enhancing reconstruction outcomes for irradiated tissue.

EXPERIMENTAL

Example 1

Adult 60-day-old male Crl:NU-Fox1NU immunocompromised mice were used for experiments in this study. Twelve mice were treated with a total of 30 Gy external beam radiation, delivered as six fractionated doses of 5 Gy each over 12 days, followed by 5 weeks of recovery. An additional six non-irradiated mice were used as healthy controls for laser Doppler analysis (LDA) and skin analysis. Irradiated mice were divided into two treatment groups: a DFO experimental group and saline control group. Following recovery, mice underwent injection of either DFO (1 mg in 100 µl saline) or 100 µl of saline alone beneath the dermis every other day for a total of seven treatments. FIG. 1 shows a schematic of this irradiated scalp treatment.

After irradiation, fat grafting was performed on the irradiated mice. After informed consent was obtained, lipoaspirate was obtained from three healthy female donors, ages 45, 49 and 51, with no other medical co-morbidities under an approved IRB protocol #2188.

Lipoaspirate was allowed to settle for 15 minutes for layers to separate by gravity sedimentation, and then oil and blood layers were removed by vacuum aspiration. The remaining fat layer was centrifuged at 1300 ref for 3 minutes at 4° C. Any remaining oil and blood was again removed and the remaining fat was transferred into lee syringes for injection through a 14-gauge needle. Fat grafting was performed beneath the scalp by creating a subcutaneous tunnel with the needle and then injecting 200 of lipoaspirate in retrograde fashion while pulling the needle out.

Laser Doppler Analysis ("LDA") was performed to measure perfusion at the irradiated site using a Perimed PIM 3 laser Doppler perfusion imager (Datavagen, Sweden). The signal generated by the LDA, laser Doppler perfusion index (LDPI), was used for comparative purposes. LDPI is a product of the blood cell velocity and concentration and is represented by a color spectrum, with black/dark blue representing low perfusion and red representing high perfusion. LDA was performed prior to irradiation, following completion of irradiation and recovery, and then twenty-four hours following each treatment with DFO or saline. LDA was also performed every two weeks after fat grafting.

Figure 2A:
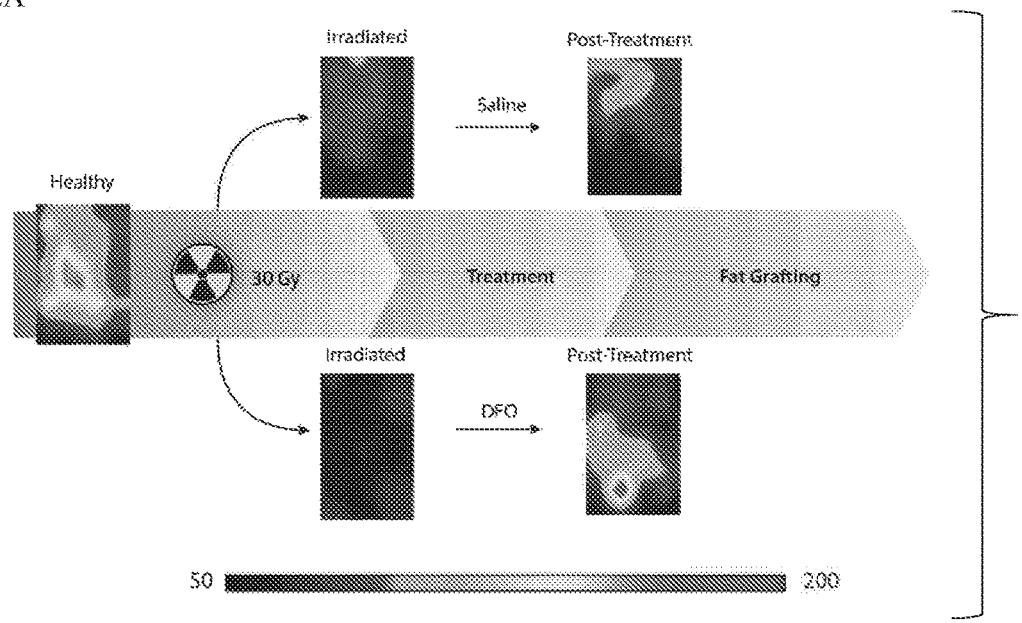
FIG. 2A shows representative photos of heat maps of mice scalps before irradiation, after irradiation, and after treatment with either saline or DFO. Darker areas represent lower perfusion and lighter areas represent higher perfusion.
Figure 2B:
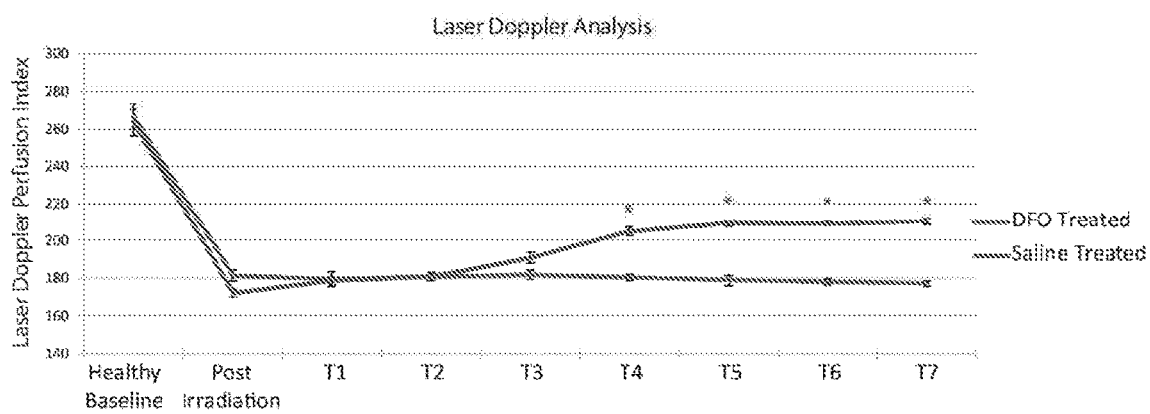
FIG. 2B shows a quantification of laser Doppler perfusion index from the irradiated mouse scalps. DFO treatments (T) caused a significance rise in perfusion after 4 treatments (T4), compared to saline injection, and plateaued after 5 treatments (T5) (*p<0.05).

Five images were taken of each mouse, and the average LDPI of the five images was recorded. FIG. 2A shows representative photos of heat maps of mice scalps before irradiation, after irradiation, and after treatment with either saline or DFO. Darker areas represent lower perfusion and lighter represent higher perfusion. FIG. 2B shows that quantification of laser Doppler perfusion index demonstrated a significant decrease in perfusion after irradiation. Laser Doppler analysis shows improved perfusion of irradiated tissue with DFO treatment. Laser Doppler analysis allows for the estimation of in vivo local blood perfusion in the microcirculation through frequency shifts in light that has been scattered by moving red blood cells. This facilitated longitudinal measurements in the same animal following each treatment with DFO. DFO treatments (T) (upper line in FIG. 2B) caused a significance rise in perfusion after 4 treatments (T4), compared to saline injection (lower line in FIG. 2B), and plateaued after 5 treatments (T5) (*p<0.05).

Mice were also imaged using a MicroCAT-11 in vivo X-Ray micro-CT scanner (Imtek, Inc.; Knoxville, Tenn.) two days after fat graft injection for baseline volume measurements. Fat graft volume retention was then analyzed every two weeks over a total of 8 weeks using microcomputed tomography, and images were reconstructed as three-dimensional surfaces through cubic-spline interpolation. All reconstructions were performed by a single investigator to avoid inter-observer variability.

For skin analysis, scalp skin biopsy was harvested from both treatment groups following completion of radiation and then 8 weeks following fat grafting. Specimens were fixed in 4% paraformaldehyde, processed, and embedded in paraffin for sectioning For dermal thickness measurement, sections were stained with hematoxylin and eosin (H&E) and imaged using a Leica DM5000 B Light microscope (Leica Microsystems; Buffalo Grove, IL) at the 20× objective. Dermal measurements were made on ten stained sections from each sample. Picrosirius red staining was also performed for collagen content. Vascularity was determined with CD31 immunofluorescent staining (1:100 Ab28364; Abcam; Cambridge, MA and 1:200 AF547; Thermo Fisher Scientific; Waltham, MA) and DAPI counterstaining to visualize cell nuclei. Fluorescent images were obtained using an X-Cite 120 Fluorescence Illumination System (Lumen Dynamics Group, Inc.; Ontario, Canada) at the 20× objective. Quantification of CD31 staining was performed using ImageJ (National Institutes of Health; Bethesda, MD), with pixel-positive area per high power field measured to determine vascular density (11). Comparisons for both dermal thickness and CD31 immunofluorescent staining were also made to non-irradiated skin.

Following completion of irradiation and five-week recovery, perfusion at the scalp was noted to significantly drop from 265.23±7.01 LDPI (pre-radiation baseline) to 176.70±2.59 LDPI (FIG. 2B). However, treatment of the scalp with 1 mg of DFO every other day after radiation recovery resulted in increased LDPI, which became significant after four treatments (205.08±2.30 LDPI) (*$p<0.05$). No increase in LDPI measurements was noted after four treatments, though, as three additional treatments of DFO did not result in any significant increase to perfusion. In contrast, injection of saline alone resulted in no change to LDPI measurements over the entire treatment course, as shown by the lower line in FIG. 2B.

For the statistical analysis, data are presented as means±SE. Two-tailed Student's t-test was used for comparison between two groups and an analysis of variance with Tukey post-hoc test was used for multiple group comparisons. All analyses were performed using StatPlus software (Analyst-Soft, Inc., Alexandria, Va.). A value of *$p<0.05$ was considered significant.

In vivo radiographic analysis of fat grafts showed DFO preconditioned irradiated mice retained more fat volume (89.24%+1.69) after two weeks compared to saline injected control mice (74.03+7.91) (FIGS. 3A-C). Fat graft volume retention was consistently greater among DFO treated mice (upper line in FIG. 3C) compared to saline control mice (lower line in FIG. 3C), and at 6 and 8 weeks, these differences were statistically significant (week 6: 73.17%±4.26 DFO vs. 52.40%±4.83 saline treated, and week 8: 71.75%±3.70 DFO vs. 49.47% 30 4.62 saline treated; *$p<0.05$).

Figure 4:
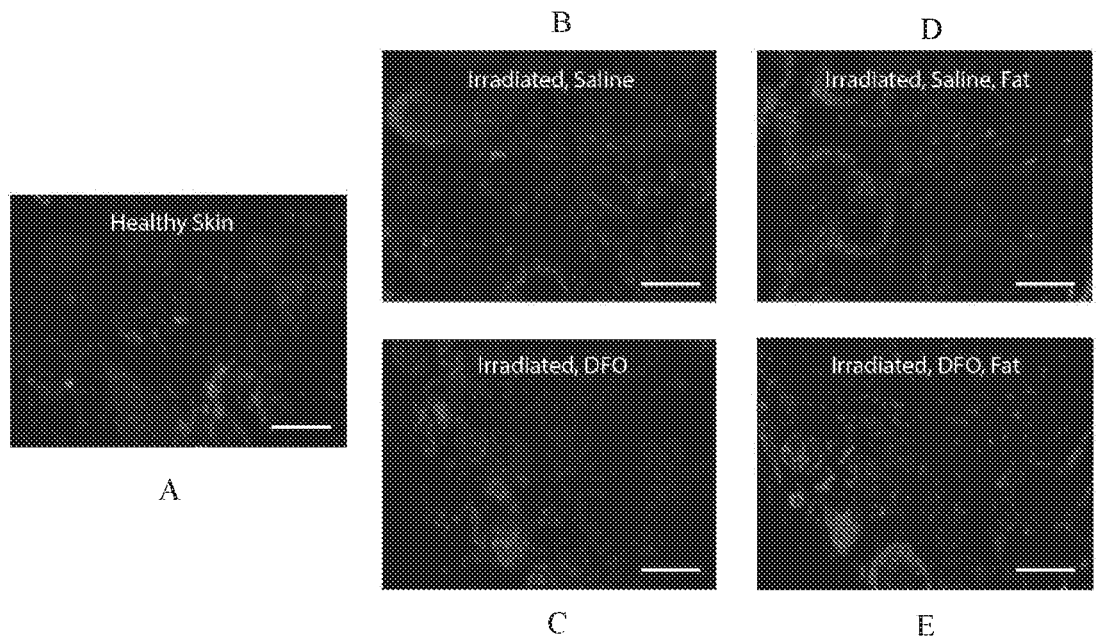
FIG. 4A-E show a histologic evaluation of irradiated scalp vascularity with representative images taken at 20× magnification of scalp skin with immunofluorescent staining for CD31 showing increased vascularity with DFO preconditioning. Scale bar represents 100 µm.

Following irradiation and saline control treatment, vascularity in skin biopsies, as demonstrated by CD31 staining, was found to be significantly lower than non-radiated healthy skin (*$p<0.05$) (FIG. 4A-E and FIG. 5). However, treatment of irradiated skin with DFO resulted in increased CD31 staining, though this did not reach healthy skin levels, as shown in FIG. 4A. As expected following fat grafting, skin biopsies obtained after 8 weeks also demonstrated increased CD31 staining compared to control, saline injected irradiated skin. Interestingly, slightly more CD31 staining following fat grafting was also noted with DFO preconditioned mice relative to saline control fat grafted mice, though this difference was not significant.

Figure 5:
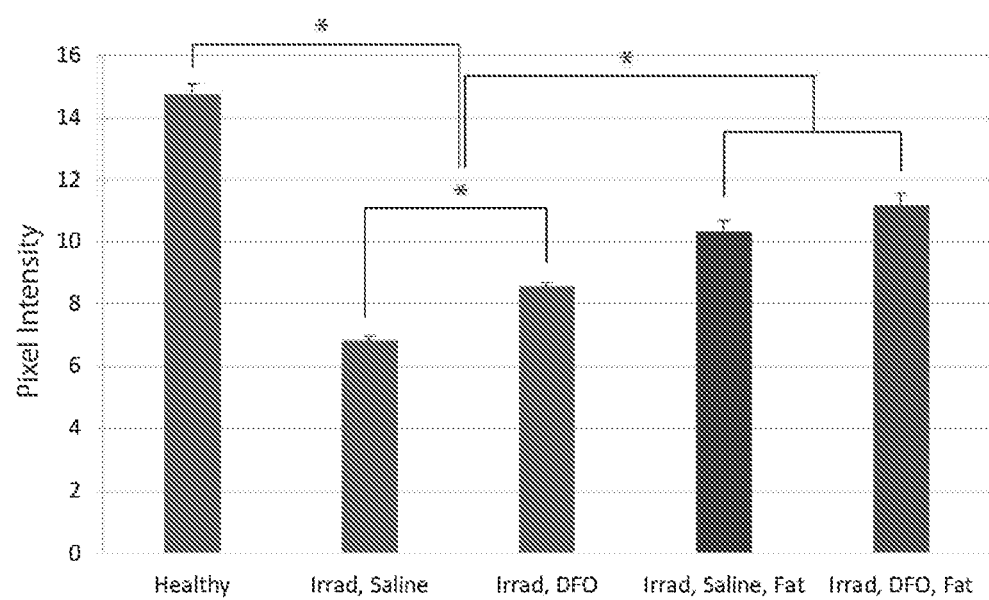
FIG. 5 shows a quantification of CD31 immunofluorescent staining revealed significant drop following irradiation. Significant improvement was noted with DFO treatment, and vascularity was further enhanced with fat grafting (*p<0.05).
Figure 6A:
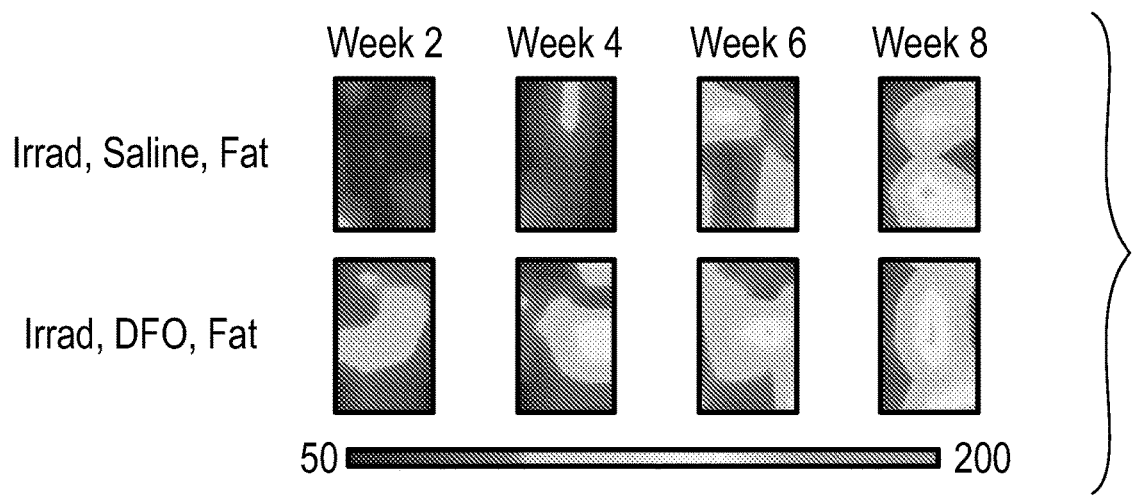
FIG. 6A shows representative LDA images of saline (top) and DFO (bottom) treated tissue scalp following fat grafting. Darker areas represent lower perfusion and lighter areas represent higher perfusion.
Figure 6B:
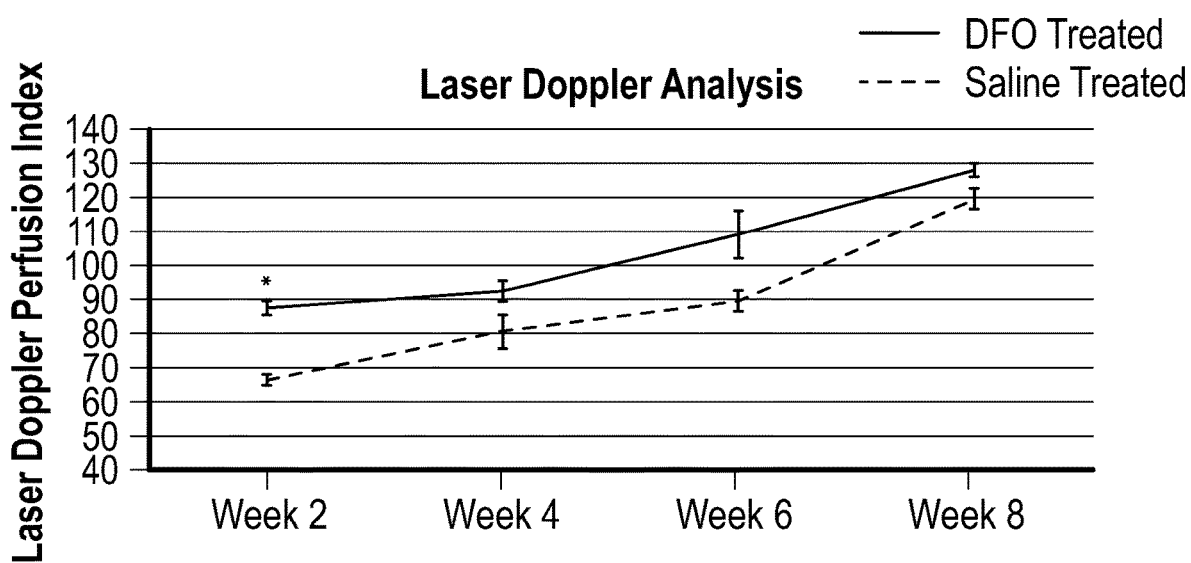
In FIG. 6B, a quantification of laser Doppler perfusion index demonstrated DFO treated scalp (upper line) had significantly higher perfusion than saline treated scalp (lower line) two weeks after fat grafting (*p<0.05). Both groups demonstrated increased perfusion after fat grafting with no significant difference appreciated after week 2.

Perfusion of the skin following fat grafting was also measured by LDA, and LDPI values were found to be lower than immediately following completion of DFO or saline preconditioning due to changes in three-dimensional architecture of the region of interest following placement of fat. However, two weeks following injection of fat grafts, significantly more perfusion was still noted in DFO preconditioned mice (86.33±2.00 vs. 65.72±2.02 LDPI for saline control; *$p<0.05$) (FIG. 5). Perfusion also continued to increase in the DFO preconditioned mice following fat grafting (upper line in FIG. 6B), but perfusion similarly increased in saline injected control mice after fat grafting (lower line in FIG. 6B), and after week 2, no significant difference on LDA was appreciated between the two groups (127.7835 2.29 vs. 119.18 ±4.09 LDPI for DFO and saline treated mice eight weeks following grafting, respectively; $p>0.05$) (FIGS. 6A-B).

Figures 7A, 7B, 7C, 7D, 7E:
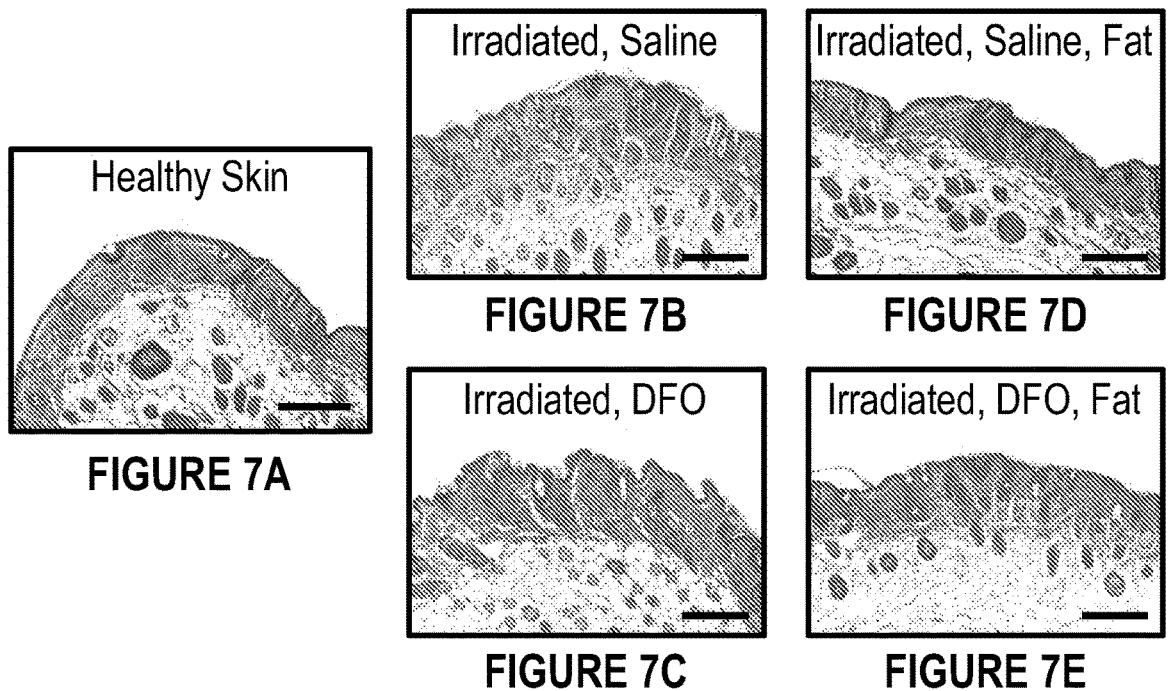
FIG. 7A-E show representative H&E stained sections at 10× magnification of non-irradiated, healthy skin, irradiated skin after saline or DFO treatment, and irradiated skin after saline or DFO treatment and fat grafting. Scale bar represents 200 µm.
Figure 8:
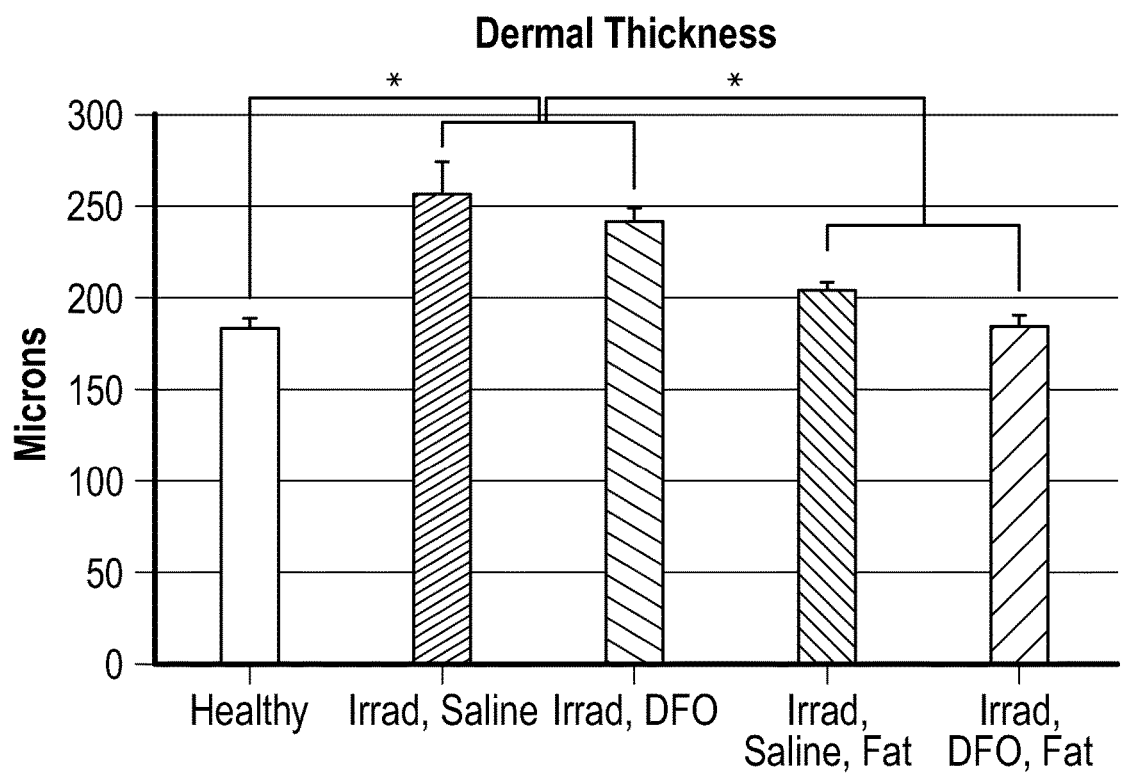
Figure 9:
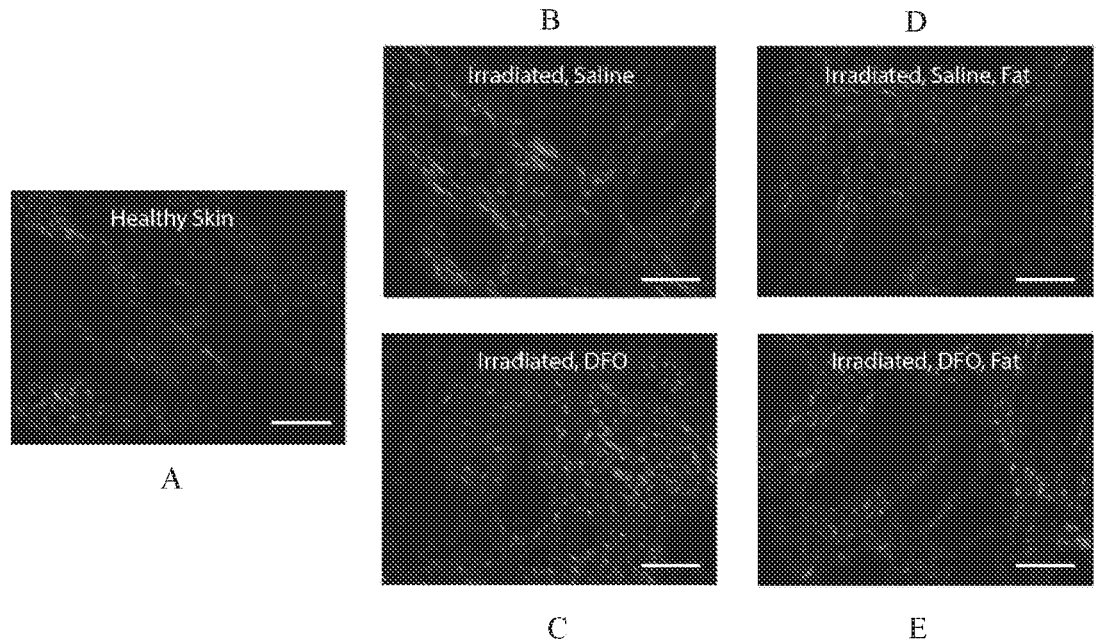
Figure 10:
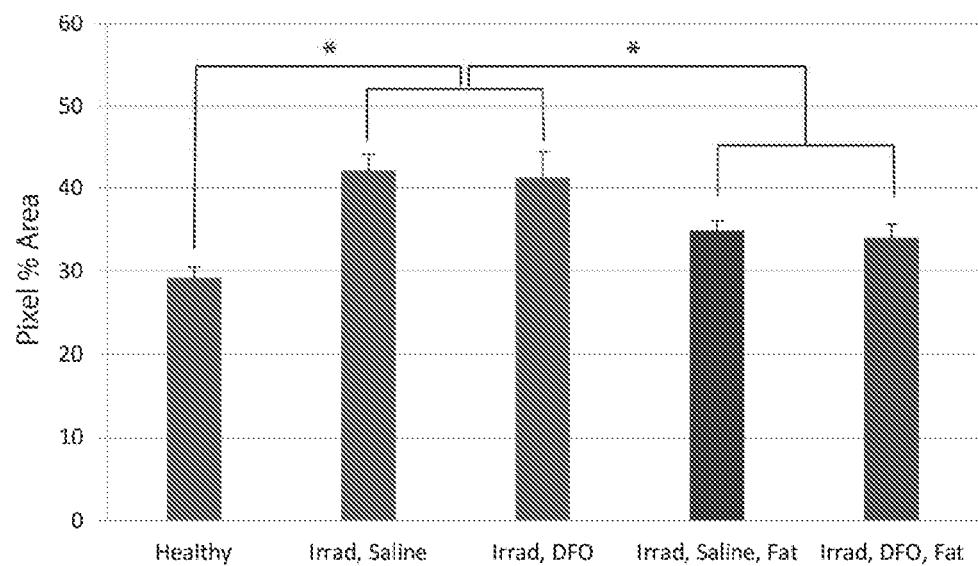

Finally, dermal thickness of irradiated skin following saline treatment was significantly greater than healthy, non-irradiated skin (*$p<0.05$) (FIGS. 7-8). Compared to saline injected mice (256.71±16.76 pm), DFO treatment on irradiated skin resulted in a slight decrease in dermal thickness, (242.09±7.22 pm) but this was not significantly less. However, fat grafting, whether into saline or DFO preconditioned sites, was found to significantly decrease dermal thickness, though there was no significant difference when comparing these two groups ($p>0.05$). Paralleling these findings, picrosirius red staining revealed significantly increased collagen content following irradiation and saline treatment (*$p<0.05$). DFO treatment on irradiated skin resulted in a slight decrease in collagen content which was not statistically significant. And similar to our observations with dermal thickness, fat grafting, whether into saline or DFO preconditioned sites, was found to significantly reduce collagen content (*$p<0.05$) (FIGS. 9-10).

Thus, local injections of DFO into irradiated hypovascular skin improved perfusion, as measured by laser Doppler analysis. Laser Doppler analysis allowed for the estimation of in vivo local blood perfusion in the microcirculation through frequency shifts in light that has been scattered by moving red blood cells. This facilitated longitudinal measurements in the same animal following each treatment with DFO. Histologic analysis of treated skin also revealed increased vascularity by CD31 staining following DFO treatment. This translated to enhanced volume retention when fat grafts were placed into DFO preconditioned recipient sites. Interestingly, the addition of fat grafts to DFO treated irradiated tissue led to further improvement in vascularity, even though DFO-related effects were seen to plateau after four treatments. This suggests that alternative mechanisms may also be employed by transferred adipocytes and associated stromal cells to improve vascularity following fat grafting. Finally, the effects of DFO treatment on skin vascularity were not found to be associated with significant changes to dermal thickness and collagen content.

Example 2

Adult 60-day-old male Crl:NU-Fox1NU immunocompromised mice were used for experiments in this study. Twelve mice were treated with a total of 30 Gy external beam radiation, delivered as six fractionated doses of 5 Gy each every other day over 12 days, followed by one month of recovery. An additional six non-irradiated mice were used as healthy controls for laser Doppler analysis (LDA) and skin analysis. Irradiated mice were divided into two treatment groups: a DFO experimental group and a control group. Following recovery, the we applied to the irradiated scalp skin of the DFO experimental group a transdermal delivery system comprising a dry film having DFO at a concentration of 13.4% weight/weight % of film encapsulated in a reverse micelle with a non-ionic surfactant stabilized by polyvinylpyrrolidine (PVP) in an ethylcellulose matrix, cut into a ⅝ inch circle and covered by a silicon sheet of the same size. Identical transdermal delivery devices, but omitting the DFO, were applied to the irradiated scalp skin of the control group mice. The transdermal delivery systems were left in place for two days, then replaced with new devices. After irradiation and treatment with seven changes of the transdermal delivery devices, fat grafting was performed on the irradiated mice, as described in Example I above.

Figure 11:
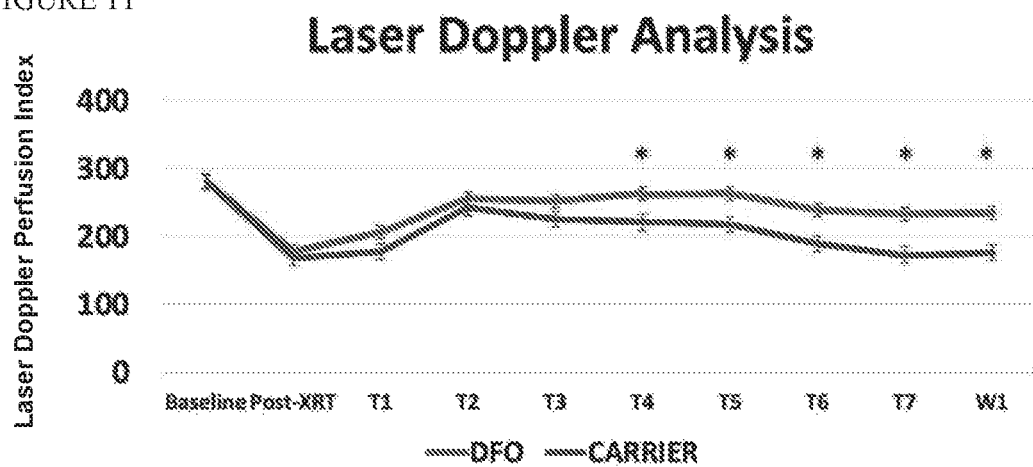
FIG. 11 shows that quantification of laser Doppler perfusion index demonstrated scalp pretreated with a DFO transdermal delivery system (upper line) had significantly higher perfusion than scalp pretreated with a transdermal delivery system lacking DFO (lower line) one week after fat grafting (*p<0.05).
Figure 12:
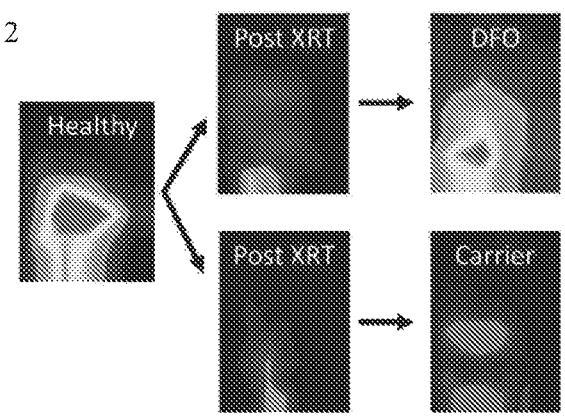
FIG. 12 shows representative LDA images of mice scalp showing perfusion in mice prior to radiation therapy (leftmost image), in an experimental group pretreated with DFO delivered by a transdermal delivery device (upper two images), and in a control group pretreated with transdermal delivery devices without DFO (lower two images) immediately after cessation of radiation therapy and one week later.

Laser Doppler Analysis ("LDA") was performed prior to and after fat grafting to measure perfusion at the irradiated site, as described above in Example 1. FIGS. 11 and 12 show that mice with the DFO transdermal delivery patches (upper line in FIG. 11) showed significant improvements in blood flow (*p<0.05) compared to mice treated with transdermal delivery devices without DFO. FIG. 11 shows that quantification of laser Doppler perfusion index demonstrated scalp pretreated with a DFO transdermal delivery system (upper line) had significantly higher perfusion than scalp pretreated with a transdermal delivery system lacking DFO (lower line) one week after fat grafting (*p<0.05). FIG. 12 shows representative LDA images of mice scalp showing perfusion in mice prior to radiation therapy (leftmost image), in an experimental group pretreated with DFO delivered by a transdermal delivery device (upper two images), and in a control group pretreated with transdermal delivery devices without DFO (lower two images) immediately after cessation of radiation therapy and one week later. Darker areas represent lower perfusion and lighter areas represent higher perfusion.

Figure 13:
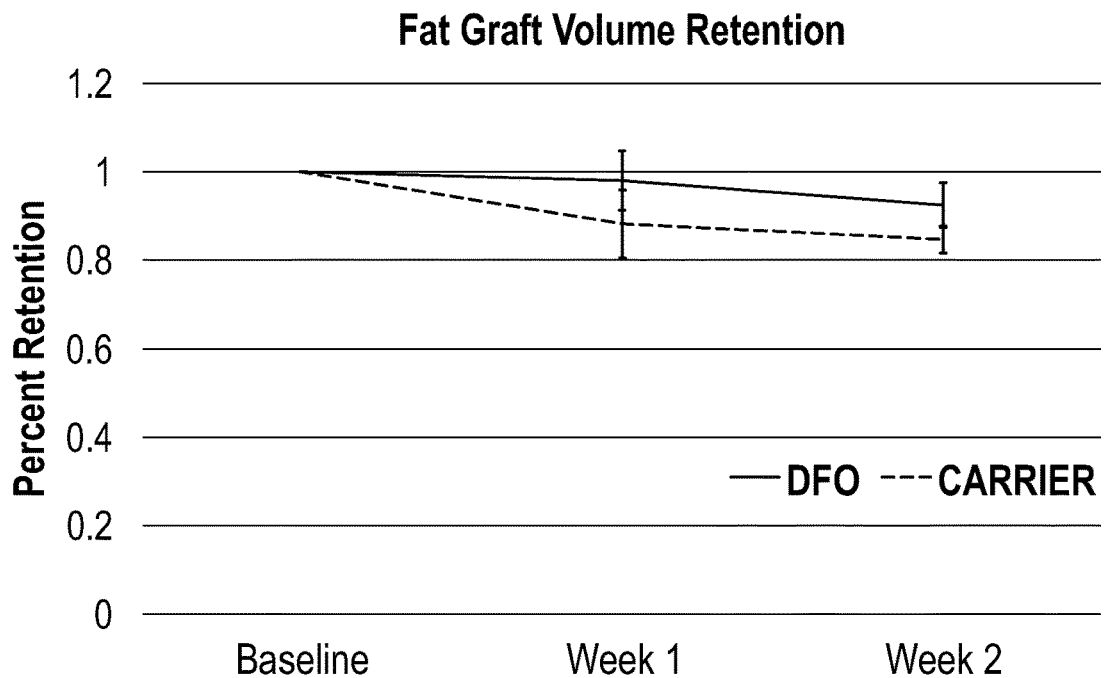
FIG. 13 shows that quantification of fat graft volumes revealed significantly increased retention in fat grafts placed into DFO treated scalp (upper line) when compared to control (no DFO) treated scalp (lower line) after one and two weeks.
Figure 14:
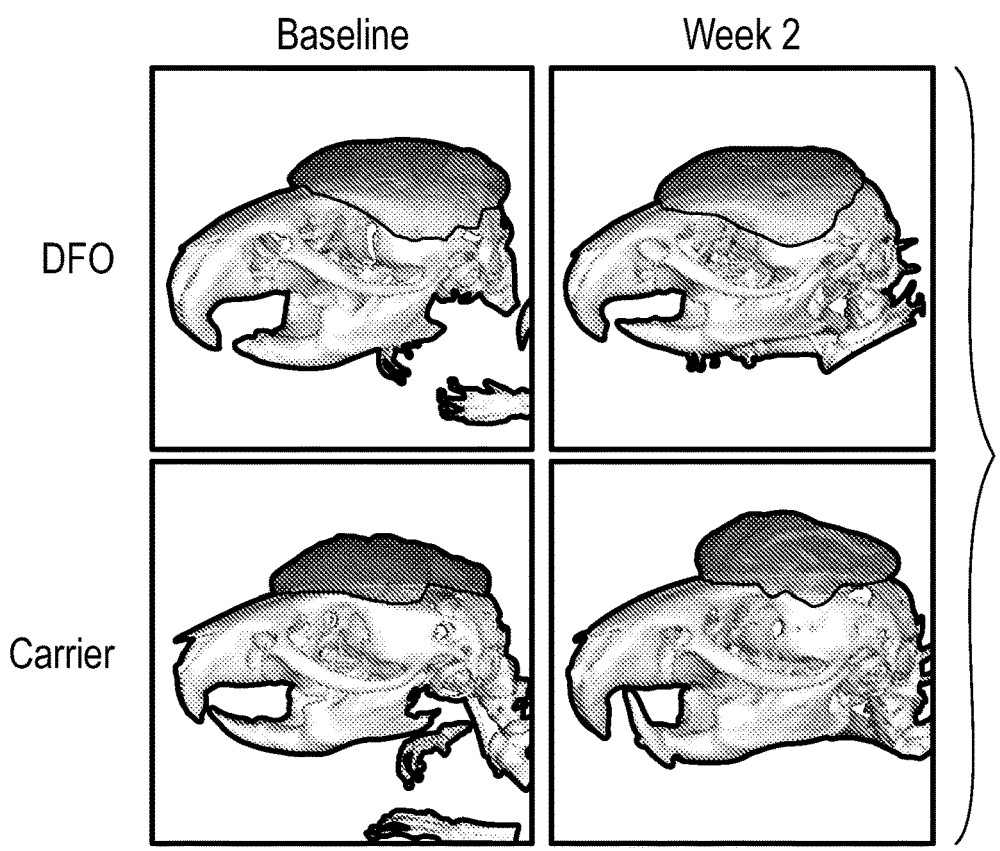
FIG. 14 shows representative three-dimensional reconstructions of fat grafts after two weeks in either DFO (upper) or control (lower) preconditioned irradiated scalp.

In vivo radiographic analysis of fat grafts showed DFO preconditioned irradiated mice retained more fat volume after two weeks compared to control mice (FIGS. 13-14). Fat graft volume retention was consistently greater among mice treated with transdermally administered DFO (upper line in FIG. 13) compared to control mice whose transdermal delivery devices lacked DFO (lower line in FIG. 13). FIG. 14 shows representative three-dimensional reconstructions of fat grafts after two weeks in either DFO (upper) or control (lower) preconditioned irradiated scalp.

Figure 15A:
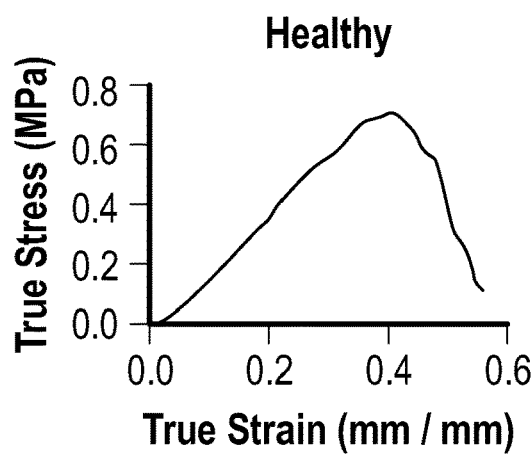
FIGS. 15A-C and 16 show skin stiffness data for healthy mice, mice treated with transdermal DFO delivery devices and mice pretreated with transdermal delivery devices without DFO.
Figure 15B:
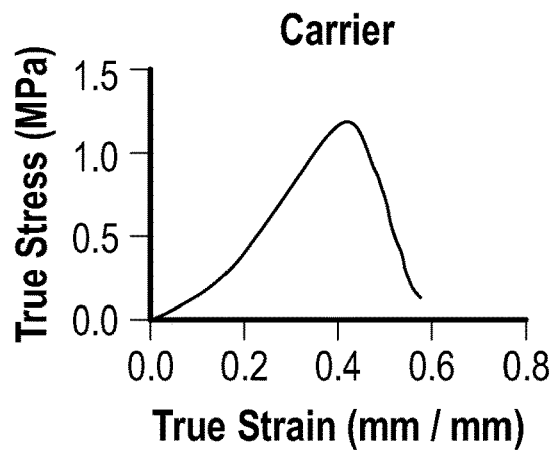
Figure 15C:
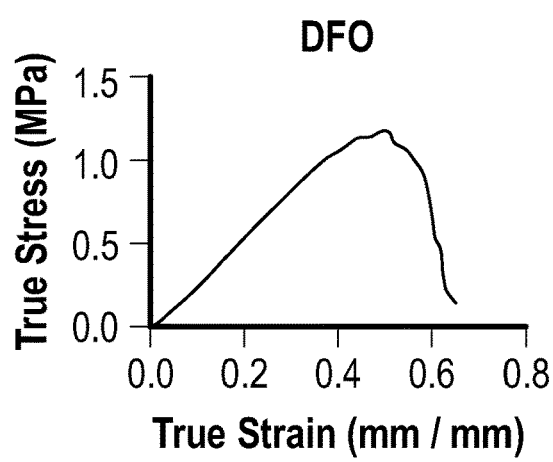
Figure 16:
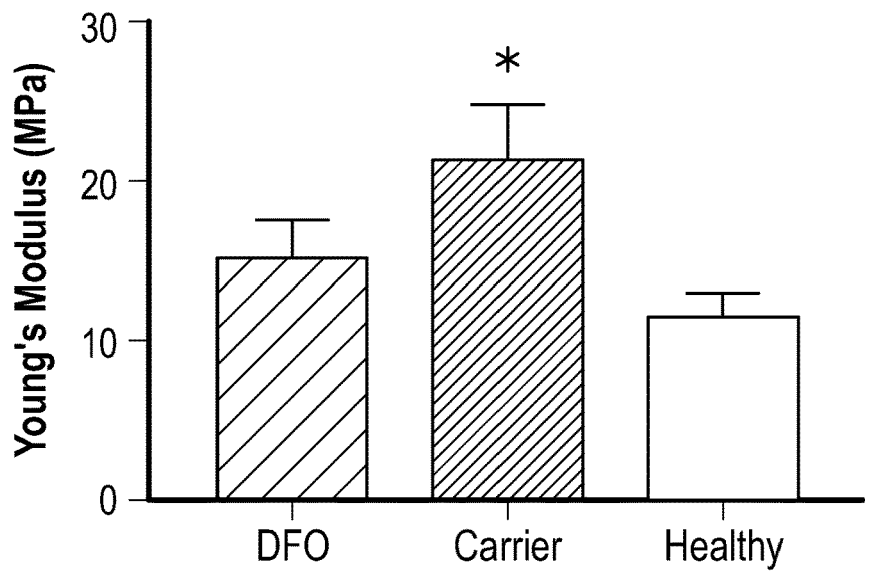

For skin analysis, scalp skin biopsy was harvested from both treatment groups following completion of radiation at the time of fat graft placement by trimming a piece of skin at the fat graft incision site. Scalp skin was also harvested from healthy mice that had not been irradiated. Skin stiffness was measured using a MTS Bionix 200 with an Interface SM-19 force transducer. Stress-strain curves were generated as shown in the figure and the Young's modulus (slope) was then calculated to figure out the stiffness. FIG. 15A shows the stress-strain curve for the healthy mice that had not been irradiated, FIG. 15B shows the stress-strain curve for the irradiated mice that had been treated with the transdermal delivery device without DFO, and FIG. 15C shows the stress-strain curve for the experimental group of irradiated mice treated with DFO via the transdermal delivery system. FIG. 16 summarizes the Young's Modulus data for the three groups. These data show that treatment of the skin with DFO after radiation therapy results in reduced skin stiffness.

Example 3

Female adult 60-day-old CD-I Nude immunocompromised mice (Crl:CDI-Foxnlnu, Charles River) were used for experimentation (total n=16). Mice were maintained at the Stanford University Research Animal Facility (4 animals/cage) in sterile micro-insulators and were given water and rodent chow ad libitum, in accordance with Stanford University guidelines. All experiments were performed under approved APLAC protocols (APLAC #31212) in accordance with the Stanford University Animal Care and Use Committee Guidelines.

Figure 17:
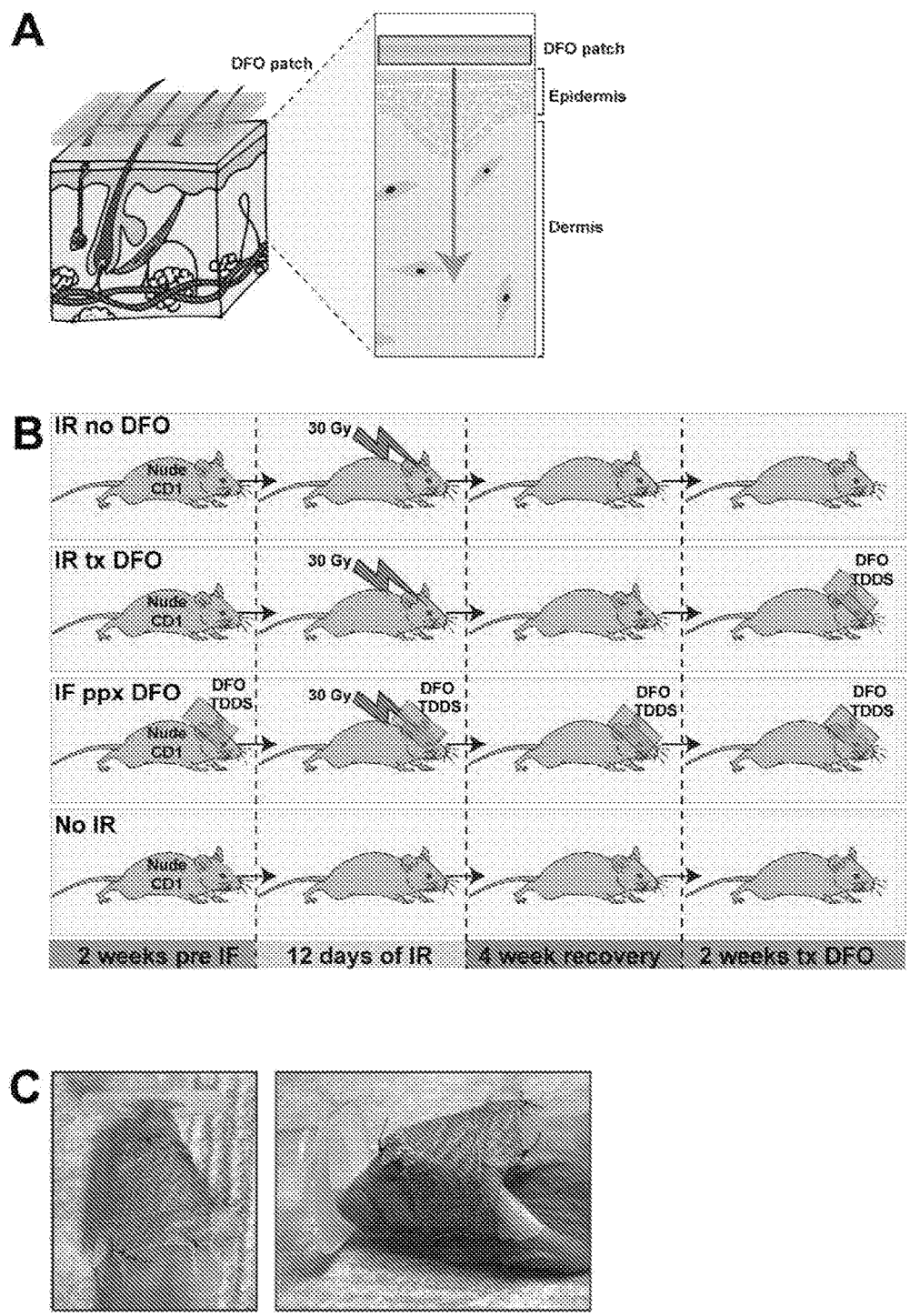
FIG. 17A shows a schematic representation of how DFO may be delivered topically via a transdermal delivery system (TDDS). DFO is contained along a monolithic layer dispersed within the biodegradable polymer and complexed with PVP to stabilize its amorphous form and promote tissue permeation over 24 hours (arrow).
FIG. 17B is a schematic representation of four experimental groups and timeline in an experiment showing prophylactic administration of DFO. Group 1 mice (row 1 of FIG. 17B) received: irradiation alone (IR no DFO). Group 2 mice (row 2 of FIG. 17B) irradiation followed by DFO treatment (IR tx DFO). Group 3 mice (row 3 of FIG. 17B) received irradiation both preceded and followed by DFO treatment (IR ppx DFO).
FIG. 17C are photographic representations of mice with the DFO patch secured. The DFO TDDS was adhered to leukotape and stabilized to the mouse scalp using thins strip of superglue at the rostral and caudal ends, and 3 anchoring sutures. The DFO TDDS in situ is shown from the aerial (left) and profile (right) views. Abbreviations for FIGS. 17A-17B are as follows: DFO—deferoxamine, Gy—gray, IR—irradiation, ppx—prophylactic, tx—therapeutic.

DFO TDDS delivery: DFO was delivered topically via a monolithic matrix-type TDDS containing DFO dispersed within a biodegradable polymer, as described in Duscher, et al., "Transdermal deferoxamine prevents pressure-induced diabetic ulcers", Proceedings of the National Academy of Sciences. 2015; 112(1):94-99, which is herein incorporated by reference in it entirety. The patches provided sustained release of the active ingredient. DFO is hydrophilic and complexed with polyvinylpyrrolidone (PVP) to stabilize its amorphous form and promote permeation throughout the skin over 24 hours, at a concentration of I mg in 100 microliters (FIG. 17A). Mice were split into four experimental groups (n=4/group): 1) irradiation alone (IR no DFO), 2) irradiation followed by DFO treatment (IR tx DFO), 3) irradiation both preceded and followed by DFO treatment (IR ppx DFO), and 4) no irradiation and no DFO (No IR) (FIG. 17B). Therapeutic DFO treatment began 4 weeks following the completion of a 12 day 30 Gy irradiation period and continued for 2 weeks. Delivery of prophylactic DFO began 2 weeks prior to the initiation of irradiation and continued until 6 weeks after completion. The DFO TDDS was affixed to leukotape for reinforcement, and attached to the mouse skin overlying the calvarium using superglue at either end, with three anchoring sutures and a band of leukotape secured under the mouse jaw (FIG. 17C). Each DFO TDDS was changed every 24 hours.

Irradiation: Mouse scalps were irradiated with 30 Gy delivered in six 5 Gy doses every alternate day, across 12 days total. Lead shielding was used to protect the rest of the body. Dosing and fractionation protocols were selected based on previous protocols generating RIF. Laser Doppler Analysis (LDA): Laser Doppler analysis (LDA) was performed to measure perfusion at the irradiated site. A Perimed PIM 3 laser Doppler perfusion imager (J.rf.11a, Sweden) was used. The signal generated by the laser Doppler analysis (laser Doppler perfusion index) was used for comparative purposes. This index is a product of the blood cell velocity and concentration, and is represented by a color spectrum, with black/dark blue representing low perfusion and red representing high perfusion. LDA was performed immediately after irradiation and 6 weeks after irradiation. Mice were anesthetized (isoflurane; 2-3% induction, 1-2% maintenance), and placed on a heat pad for 5 minutes before measurements were taken in the region of interest (RO1) across the mouse scalp (FIG. 18A). Five images were taken of each mouse and the average laser Doppler perfusion index of the five images was recorded, to give a single mean value per mouse.

Histology: Six weeks following irradiation, mice were sacrificed, and the scalp skin was processed for histological analysis. Specimens were fixed in 4% paraformaldehyde (PFA, Electron Microscopy Sciences, Cat #15710) at 4° C. for 18 hours, processed, and embedded in paraffin for sectioning For assessment of dermal thickness sections were stained with Hematoxylin and Eosin (H&E, Abeam, Cambridge, Mass., ab245880), and for assessment of collagen fiber networks, sections were stained with Picrosirius Red (Abeam, ab150681) using standard protocols. The dermis was defined as the vertical distance from the basal layer of the epidermis to the underlying hypodermis and was measured on 10 randomly chosen sections per mouse per condition at the 20× objective. For assessment of collagen fiber networks, Picrosirius- stained skin was imaged (FIG. 20A bottom row) using polarized light and the 40× objective (25 images per mouse for a total of 100 images per condition). Slides were imaged using the Leica DM5000 Blight microscope (Leica Microsystems, Buffalo Grove, Ill.). To assess vascularity, immunostaining for mouse endothelial cells was performed. Paraffin slides were blocked with 1× Powerblock (Biogenex, HK083-50K) and incubated for 1 hour at 37° C. with unconjugated anti-mouse CD31 (PECAM, Abeam, Ab28364) at a 1:100 dilution in 0.1× Powerblock. Specimens were washed in phosphate buffered saline (PBS, Gibco®, 10010023), incubated with Alexa Fluor 647 conjugated secondary antibody (Abeam, Ab10079) for 1 hour at 37° C., washed in PBS, and then mounted onto glass slides in DAPI Fluromount-G (SouthernBiotech, 0100-20). Fluorescent images were taken using the LSM 880 inverted confocal (Airyscan, GaAsP detector, 880, Beckman), using standard field (1024×1024) for all images.

Figure 20A:
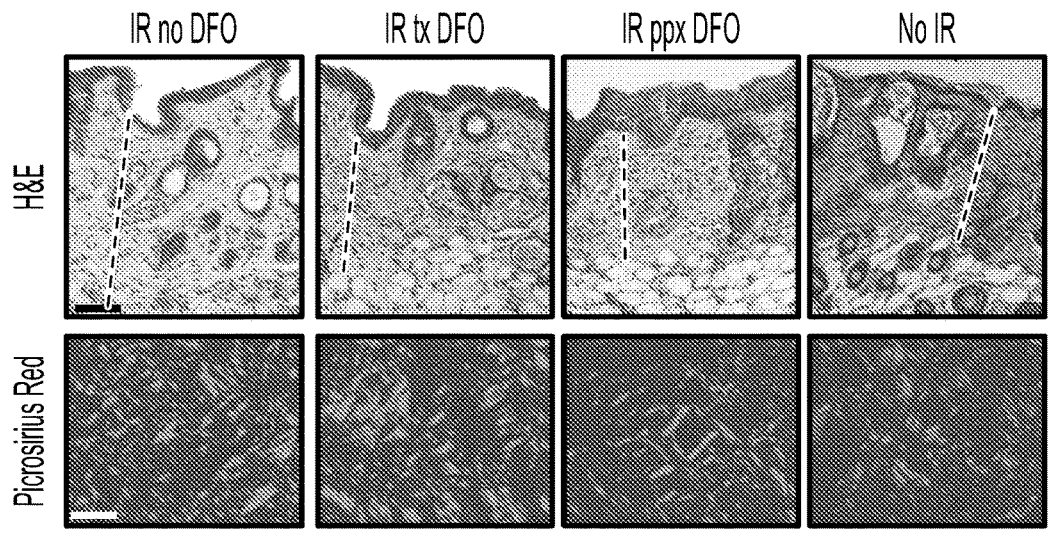
FIG. 20A is photographic representations of stained skin sections including Hematoxylin and Eosin- (top row) and Picrosirius Red-stained tissue sections, showing the histological structure and collagen fiber networks in mice of all the four treatment groups. Error bars: 100 µm (top row), 50 µm (bottom row). Black dotted lines show the dermal thickness.
Figure 20B:
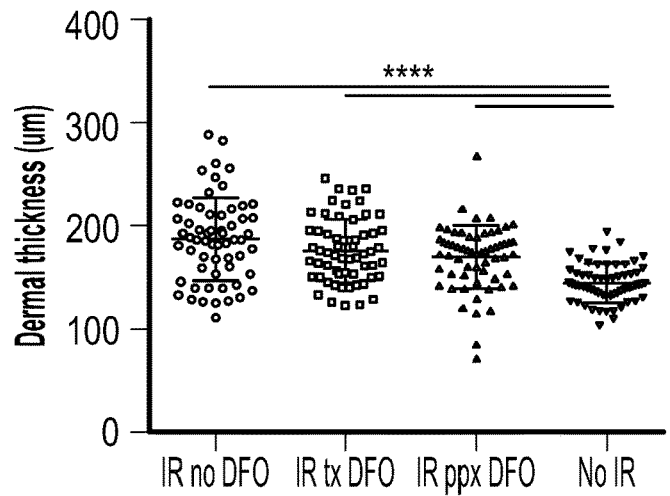
FIG. 20B is a graphical representation of quantification of dermal thickness in mice of all four treatment groups. Non irradiated skin was thinner than irradiated skin (all ****$p<0.0001$), and DFO treatment tended to decrease dermal thickness, with the greatest benefit found in mice receiving continuous DFO treatment compared to DFO post irradiation only.
Figure 20C:
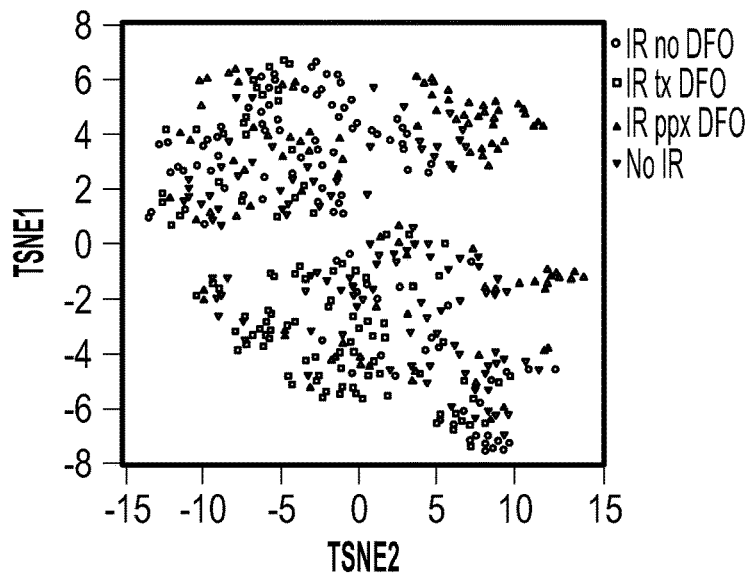
FIG. 20C is a graphical representation of a T-Distributed Stochastic Neighbor Embedding (TSNE) plot representing the grouping of collagen fiber network parameters in mice of all four conditions. The collagen fibers in the skin mice receiving continuous DFO treatment ('IR ppx DFO'; red) appeared the most distinct and clustered together at the far right of the TSNE plot. Abbreviations used within the FIGS. 20A-20C are as follows: DFO—deferoxamine, H&E—hematoxylin and eosin, IR—irradiation, ppx—prophylactic, tx—therapeutic.

Statistical Analysis: Data are presented as mean and standard error of the mean (SEM) when parametric, and as median and range when non-parametric. Images of Picrosirius Red-stained slides were color deconvoluted, converted to gray scale, binarized, and skeletonized using a novel algorithm run in MATLAB (R2018b, MathWorks, Natick, MA) 0.24 From the skeletonized images, 13 parameters of collage fibers were extracted (including length, width, branchpoints, brightness) and underwent dimensionality reduction to generate 2 dimensional t-Distributed Stochastic Neighbor Embedding (TSNE) plots to visualize collective differences in the collagen fiber network patterns between groups. Quantification of CD31 staining was performed using ImageJ (National Institutes of Health, Bethesda, MD) on three images per mouse per condition, with pixel-positive area per high-power field measured within the dermis to determine vascular density (FIG. 20C). The Mann-Whitney test (non-parametric) was used to compare means between two groups, and the Kruskal-Wallis test (non-parametric) was used to compare means across three or more groups, using the PRISM (Graphpad) software. A value of $*p<0.05$ was considered statistically significant. The TSNE plot indicated that the collagen fibers in the skin mice receiving continuous DFO treatment appeared the most distinct, and may represent more post-irradiation remodeling.

DFO pre-treatment improves tissue perfusion following RT: Tissue perfusion measurements obtained by LDA immediately following RT showed that prophylactic treatment with TDDS DFO significantly mitigated the detrimental effects of RT on skin perfusion ($p<0.01$) (FIGS. 18B and 18C). Six weeks following RT, both prophylactic DFO and therapeutic DFO tended to have improvements in perfusion (FIGS. 18B and 18D). As expected, irradiated mice receiving no DFO had significantly worse scalp perfusion than the non-irradiated mice ($p<0.01$).

Figure 19:
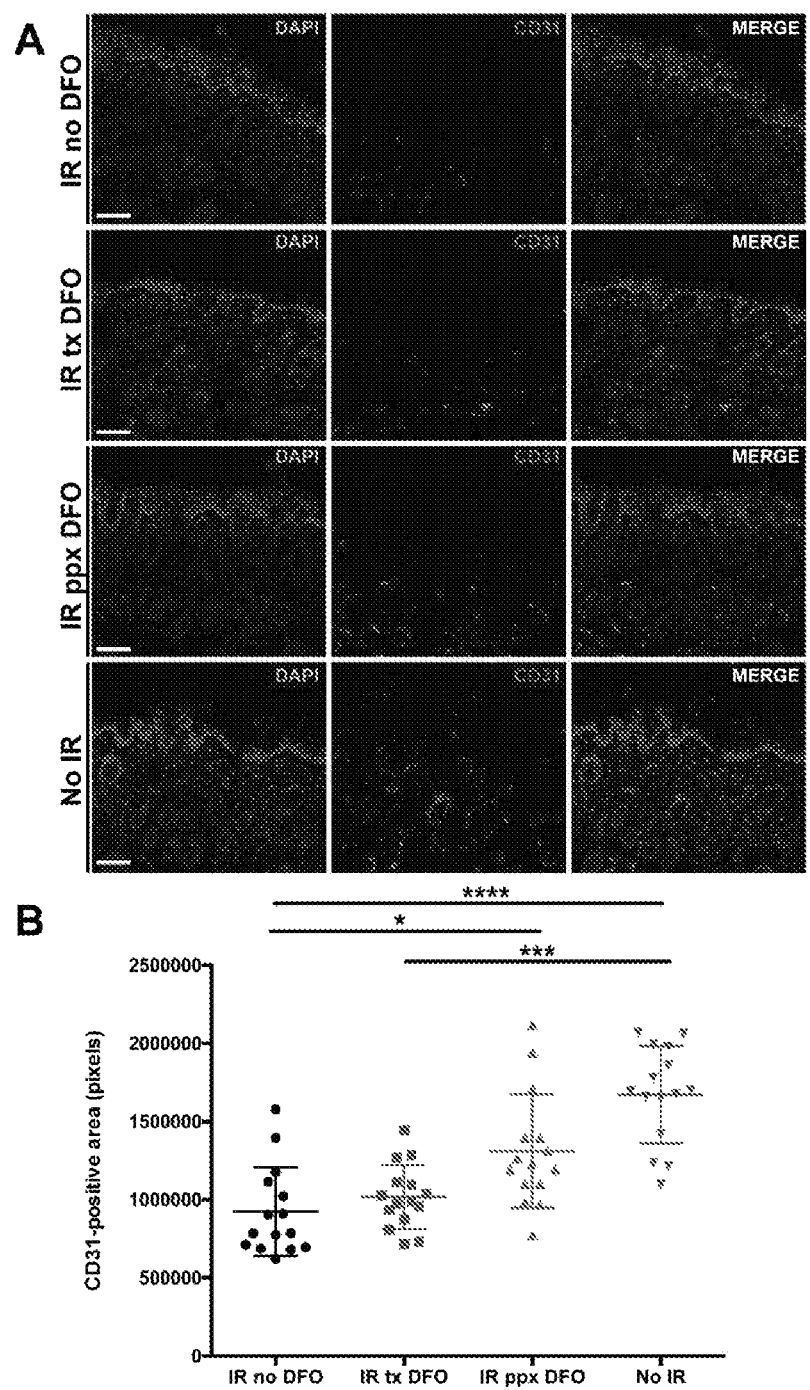
FIG. 19A is photographic representations of Immunohistochemical staining showing vascular density in all four groups of mice. Endothelial cells were stained with CD31 (PECAM, red) and nuclei were stained with DAPI (blue). Scale bar 100 µm.
FIG. 19B is a graphical representation of the quantification of mean pixels positive for CD31 in all four groups of mice. The skin of non-irradiated mice was significantly more vascularized than the skin of irradiated mice receiving no DFO treatment (**$p<0.0001$) and DFO post irradiation only (*$p<0.001$). The skin of mice receiving continuous DFO treatment was significantly more vascularized than the skin of irradiated mice receiving no DFO (*$p<0.05$). The abbreviations in FIGS. 19A-19B are as follows: DFO—deferoxamine, IR—irradiation, ppx—prophylactic, tx—therapeutic.

DFO Enhances Neovascularization: As expected, the skin of non-irradiated mice was significantly more vascularized than the skin of untreated irradiated mice ($****p<0.0001$). Skin from mice receiving prophylactic DFO was similarly well-vascularized compared to that of non-irradiated mice, and significantly more vascularized than the skin of irradiated mice not receiving any DFO ($*p<0.05$). In contrast, the skin of mice only receiving DFO post irradiation had significantly less vascularization than the skin of non-irradiated mice ($***p<0.001$) (FIGS. 19A and 19B).

DFO Enhances Dermal Thickness and Reduces Total Collagen Content: To evaluate whether DFO TDDS treatment could mitigate RIF in the skin, mouse scalp skin was harvested six weeks following irradiation for histological assessment of dermal thickness and collagen fiber networks. Analysis of hematoxylin-stained skin revealed that irradiation significantly increased dermal thickness (all $****p<0.0001$), and the dermis of irradiated but DFO-treated skin was more similar to non-irradiated skin with the mice receiving continuous DFO treatment showing the greatest benefit (FIGS. 20A [top row] & 20B).

DFO Treatment Results in Remodeling of Collagen Fiber Networks: The collagen fiber networks in mouse scalp skin were stained using Picrosirius Red (FIG. 20A bottom row), modelled using a novel computational algorithm and represented in 2 dimensional space suing a T-Distributed Stochastic Neighbor Embedding (TSNE plot) (FIG. 20C) The TSNE plot indicated that the collagen fibers in the skin mice receiving continuous DFO treatment appeared the most distinct, perhaps suggesting more post-irradiation remodeling.

Prophylactically treating mice with DFO resulted in significant benefits to scalp perfusion in the immediate post-RT period. Furthermore, prophylactic treatment was significantly more effective than post-radiation treatment alone.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be cojointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values),+/−10% of the stated value (or range of values), etc. Any numerical values given herein should also be understood to include about or approximately that value, unless the context indicates otherwise. For example, if the value "10" is disclosed, then "about IO" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of decreasing radiation induced fibrosis, the method comprising:
    administering an effective amount of deferoxamine (DFO) transdermally to a region of skin of a subject at a treatment site for a first period of time prior to a radiation treatment;
    administering an effective amount of DFO to the region of skin during a second period of time;
    administering radiation to the region of skin during the second period of time; and
    administering an effective amount of DFO to the region of skin for a third period of time subsequent to the radiation treatment,
    wherein the first period of time is 3 days to 21 days,
    wherein the second period of time is 5 days to 70 days,
    wherein the third period of time is 2 weeks to 8 weeks.

2. The method of claim 1, wherein administering the effective amount of DFO transdermally to the region of skin comprises applying a transdermal delivery device to a surface of the region of skin at the treatment site.

3. The method of claim 2, wherein the transdermal delivery device comprises DFO encapsulated in reverse micelles.

4. The method of claim 2, wherein applying the transdermal delivery device to the surface of the region of skin at the treatment site further comprises applying a new transdermal delivery device at a selected interval of time during each of the first, second and third periods of time.

5. The method of claim 4, wherein the selected interval of time is 12 hours to 36 hours.

6. The method of claim 4, wherein the selected interval of time is daily.

7. The method of claim 1, wherein administering the radiation during the second period of time further comprises administering the radiation in a pattern of administering radiation for a first portion of the second period of time and subsequently not administering radiation for a second portion of the second period of time.

8. The method of claim 7, wherein the pattern of administering radiation and subsequently not administering radiation is repeated 3 to 10 times during the second period of time.

9. The method of claim 8, wherein the first portion of time during the second period of time is 3 days to 7 days, and the second portion of time is 4 days to 10 days.

* * * * *